United States Patent [19]

Karanewsky et al.

[11] Patent Number: 4,555,506

[45] Date of Patent: Nov. 26, 1985

[54] PHOSPHORUS CONTAINING COMPOUNDS AND USE AS HYPOTENSIVES

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 334,271

[22] Filed: Dec. 24, 1981

[51] Int. Cl.[4] ........................ C07F 9/65; A61K 31/40
[52] U.S. Cl. .................................. 514/91; 548/112; 548/113; 548/23; 549/6
[58] Field of Search ............ 260/326.51, 944, 961; 424/200, 222, 211; 548/112; 514/91

[56] References Cited

U.S. PATENT DOCUMENTS

| | | | |
|---|---|---|---|
| 3,577,446 | 5/1971 | Rakhit | 260/944 X |
| 4,053,651 | 10/1977 | Ondetti et al. | 424/319 |
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 260/326.2 |
| 4,154,935 | 5/1979 | Ondetti et al. | 546/189 |
| 4,168,267 | 9/1979 | Petrillo | 200/936 |
| 4,192,878 | 3/1980 | Ondetti | 424/270 |
| 4,199,512 | 4/1980 | Ondetti et al. | 260/326.12 R |
| 4,217,359 | 8/1980 | Krapcho | 424/274 |
| 4,234,489 | 11/1980 | Ondetti et al. | 260/326.42 |
| 4,256,751 | 3/1981 | Hayashi et al. | 424/258 |
| 4,310,461 | 1/1982 | Krapcho et al. | 260/326.2 |
| 4,316,905 | 2/1982 | Krapcho | 424/274 |
| 4,337,201 | 5/1982 | Petrillo | 548/413 |
| 4,374,131 | 2/1983 | Petrillo | 424/200 |
| 4,379,146 | 4/1983 | Greenlee et al. | 424/177 |
| 4,396,772 | 8/1983 | Petrillo | 548/414 |

FOREIGN PATENT DOCUMENTS

| | | |
|---|---|---|
| 868532 | 6/1978 | Belgium . |
| 9183 | 4/1980 | European Pat. Off. . |
| 2027025 | 2/1980 | United Kingdom . |
| 2028327 | 3/1980 | United Kingdom . |
| 2039478 | 8/1980 | United Kingdom . |
| 2048863 | 12/1980 | United Kingdom . |

Primary Examiner—Glennon H. Hollrah
Assistant Examiner—D. B. Springer
Attorney, Agent, or Firm—Lawrence S. Levinson; Stephen B. Davis

[57] ABSTRACT

Phosphorus containing compounds of the formula

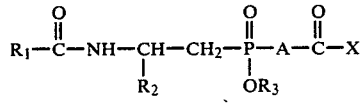

wherein X is a substituted or unsubstituted imino or amino acid and A is

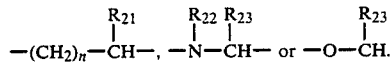

These compounds possess angiotensin converting enzyme activity and are thus useful as hypertensive agents.

7 Claims, No Drawings

PHOSPHORUS CONTAINING COMPOUNDS AND USE AS HYPOTENSIVES

BACKGROUND OF THE INVENTION

Thorsett, et al. in European Patent Application Ser. No. 9,183 disclose phosphoryl derivatives of aminoacids including proline. These compounds are disclosed as being hypotensive agents due to their angiotensin converting enzyme inhibition activity.

Petrillo in U.S. Pat. No. 4,168,267 discloses that various phosphinylalkanoyl subtituted prolines are useful as hypotensive agents due to their ability to inhibit the angiotensin converting enzyme.

Ondetti et al. in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al. in U.S. Pat. No. 4,105,776 disclose such compounds wherein the proline ring is unsubstituted or substituted by an alkyl or hydroxy group. Ondetti et al in U.S. Pat. No. 4,154,935 disclose such compounds wherein the proline ring is substituted with one or more halogens. Ondetti et al. in U.K. Patent Application No. 2,028,327 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.K. Patent Application No. 2,039,478 discloses compounds wherein the proline ring has a diether, dithioether, ketal or thioketal substituent in the 4-position. Krapcho in U.S. Ser. No. 164,985 filed July 1, 1980, now U.S. Pat. No. 4,316,905, discloses such compounds wherein the proline ring has a cycloalkyl, phenyl, or phenyl-lower alkylene substituent. Ondetti et al. in U.S. Pat. No. 4,234,489 disclose such compounds wherein the proline has a keto substituent in the 5-position. Krapcho et al. in U.S. Ser. No. 162,341 filed June 23, 1980, now U.S. Pat. No. 4,310,461, disclose such compounds wherein the proline has an imido, amido, or amino substituent in the 4-position. Iwao et al. in U.K. Patent Application No. 2,027,025 disclose such compounds wherein the proline has an aromatic substituent in the 5-position. Ondetti et al. in U.S. Pat. Nos. 4,053,651 and 4,199,512 disclose that mercaptoacyl derivatives of various aminoacids other than proline are also useful angiotensin converting enzyme inhibitors.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgium Pat. No. 868,532.

Mercaptoacyl derivatives of dihydroisoindole carboxylic acids and tetrahydroisoquinoline carboxylic acids are disclosed as being useful hypotensive agents by Ondetti et al., in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

SUMMARY OF THE INVENTION

This invention is directed to new phosphorus containing compounds of formula I and salts thereof

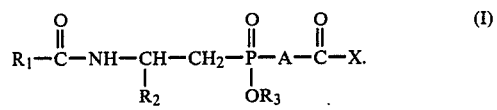

$R_1$ and $R_2$ are independently selected from hydrogen, lower alkyl, halo substituted lower alkyl,

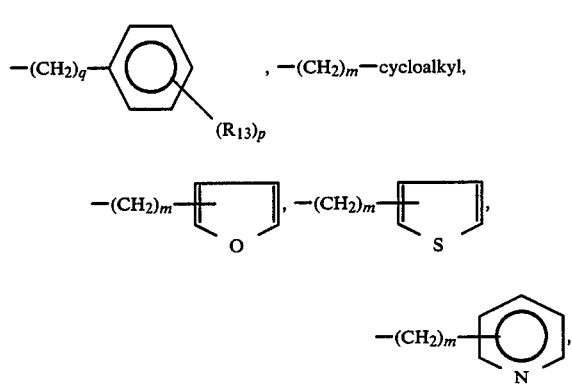

and amino substituted lower alkyl.

A is

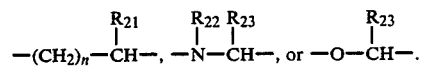

n is zero or one.

q is zero or an integer from 1 to 7.

$R_{21}$ is hydrogen, lower alkyl, halo substituted lower alkyl, benzyl, or phenethyl.

$R_{22}$ is hydrogen or lower alkyl.

$R_{23}$ is hydrogen, lower alkyl, halo substituted lower alkyl,

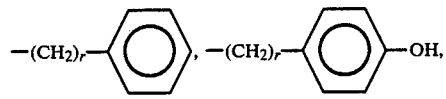

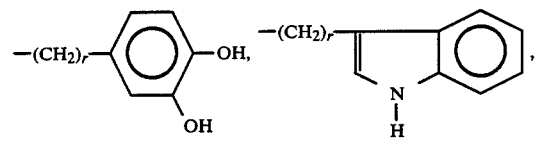

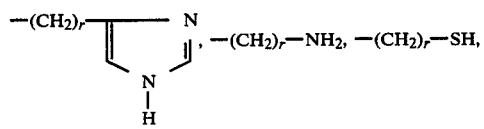

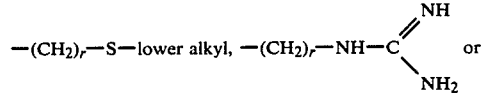

-continued
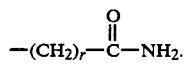
X is an imino or amino acid of the formula
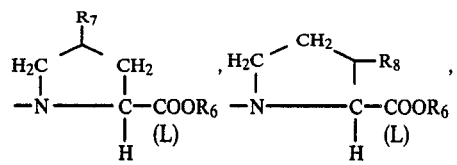
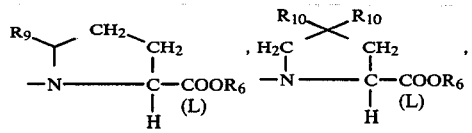
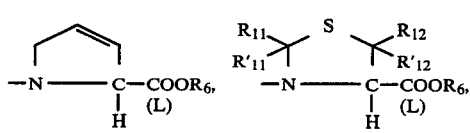
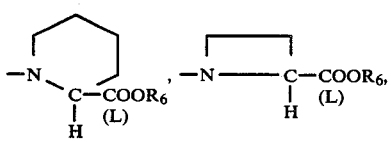
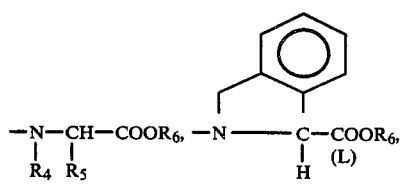
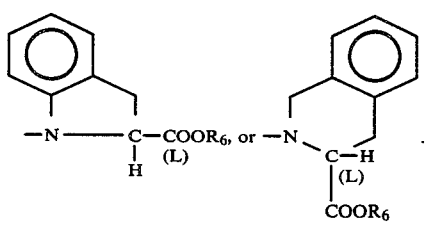
$R_7$ is hydrogen, lower alkyl, halogen, keto, hydroxy,
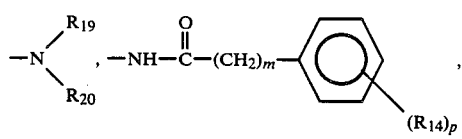
azido, amino,
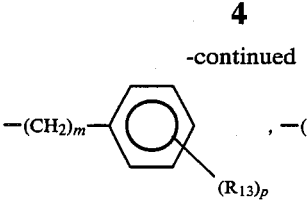
-continued
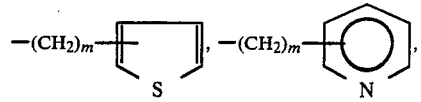
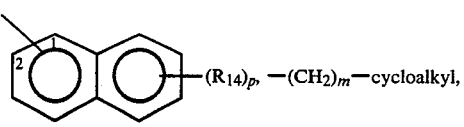
a 1- or 2-naphthyl of the formula
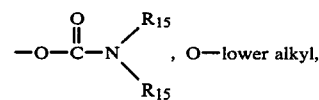
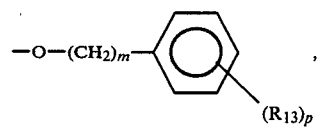
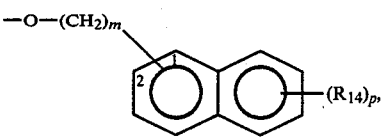
a 1- or 2-naphthyloxy of the formula
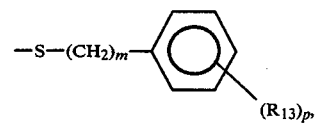
—S—lower alkyl,
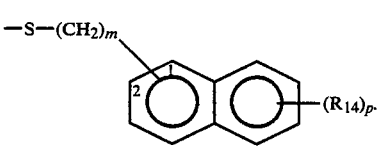
or a 1- or 2-naphthylthio of the formula
$-S-(CH_2)_m$
$R_8$ is keto, halogen,
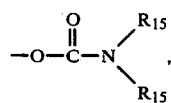

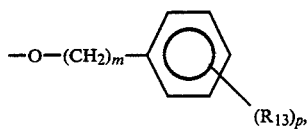

—O—lower alkyl, a 1- or 2-naphthyloxy of the formula

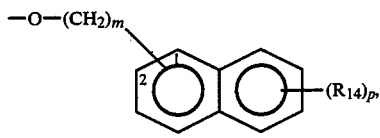

—S—lower alkyl,

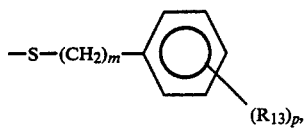

or a 1- or 2-naphthylthio of the formula

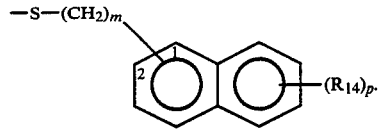

$R_9$ is keto or

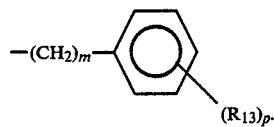

$R_{10}$ is halogen or —Y—$R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

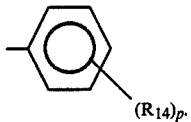

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

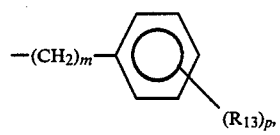

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl, cycloalkyl, or

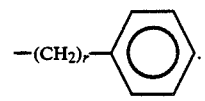

$R_5$ is hydrogen, lower alkyl,

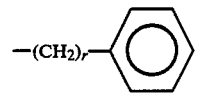

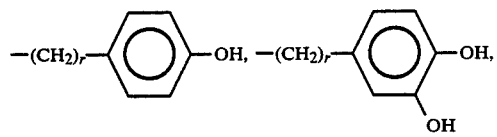

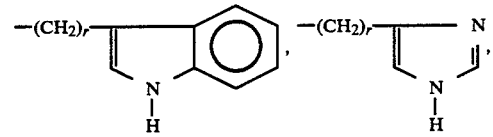

—$(CH_2)_r$—$NH_2$, —$(CH_2)_r$—$SH$,

—$(CH_2$—$S$—lower alkyl, —$(CH_2)_r$—NH—C$\begin{array}{c}\diagup NH \\ \diagdown NH_2\end{array}$ , or

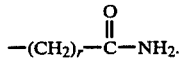

r is an integer from 1 to 4.

$R_3$ and $R_6$ are independently selected from hydrogen, lower alkyl, benzyl, benzhydryl, or

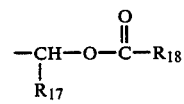

wherein $R_{17}$ is hydrogen, lower alkyl, or phenyl, and $R_{18}$ is hydrogen, lower alkyl, lower alkoxy, phenyl, or $R_{17}$ and $R_{18}$ taken together are —$(CH_2)_2$-, —$(CH_2)_3$—, —CH=CH, or

$R_{19}$ is lower alkyl, benzyl, or phenethyl.
$R_{20}$ is hydrogen, lower alkyl, benzyl or phenethyl.

DETAILED DESCRIPTION OF THE INVENTION

This invention in its broadest aspects relates to the phosphorus containing substituted imino or amino acid compounds of formula I above, to compositions containing such compounds and to the method of using such compounds as anti-hypertensive agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to lower alkyl groups in which one or more hydrogens have been replaced by $-NH_2$, i.e. aminomethyl, 2-aminoethyl, etc.

The symbols

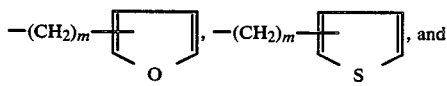, and

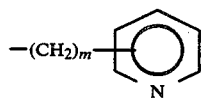

represent that the alkylene bridge is attached to an available carbon atom.

The compounds of formula I wherein A is

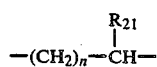

may be prepared according to the following procedure. An acrylic acid of the formula

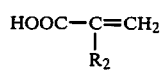    (II)

is reacted with a dichlorophosphine of the formula

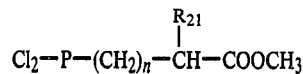    (III)

by heating in the presence of acetic anhydride and an alcohol of the formula

    (IV)

wherein $R_3$ is lower alkyl, benzyl or benzhydryl to yield the phosphinic intermediate of the formula

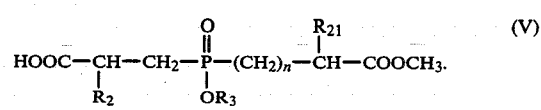    (V)

The phosphinic acid ester intermediate of formula V is then converted to the acid azide for example by treatment with azidotrimethylsilane and a coupling agent such as 1,1-carbonyldiimidazole. The resulting acyl azide intermediate is subjected to Curtius rearrangement by heating in an inert organic solvent such as toluene to give the corresponding isocyanate which is then, within isolation, reacted with the alcohol of the formula

    (VI)

wherein $R_{24}$ is benzyl or tert-butyl to yield the diester intermediate of the formula

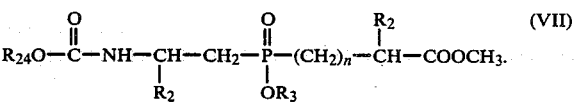    (VII)

The diester intermediate of formula VII can then be treated with trifluoroacetic acid or with hydrogen in the presence of palladium on carbon followed by reaction with the acid chloride of the formula

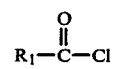    (VIII)

to yield the diester of the formula

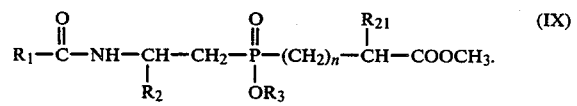    (IX)

The diester of formula IX can then be treated with base to yield the corresponding carboxylic acid and this acid or its activated form is coupled with an imino or amino acid or ester of the formula

    (X)

to yield the products of formula I. The term activated form refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably the reaction is performed in the presence of a coupling agent such as 1,1-carbonyldiimidazole, thionyl chloride, or dicyclohexylcarbodiimide.

In the above reactions, if $R_2$ is amino substituted lower alkyl then the amino group is protected for example by t-butoxycarbonyl, i.e.,

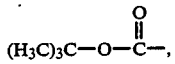

until completion of the coupling reaction after which it is removed by treatment with trifluoroacetic acid. Similarly, if $R_1$ is amino substituted lower alkyl then this amino group is protected for example by benzyloxycarbonyl, i.e.

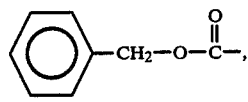

until completion of the coupling reaction after which it is removed by hydrogenation.

Also, in the above reactions if $R_5$ is

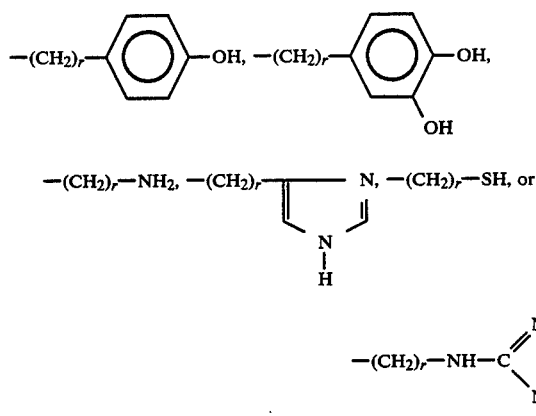

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The products of formula I wherein A is

i.e. n is zero, are preferably prepared as follows. The protected amine of the formula

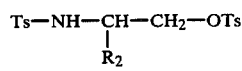

wherein Ts is tolylsulfonyl, i.e.,

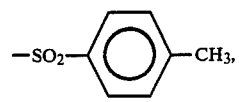

is reacted with the phosphinic acid ester sodium salt of the formula

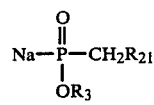

(XII)

wherein $R_3$ is lower alkyl, benzyl, or benzhydryl to yield the intermediate of the formula

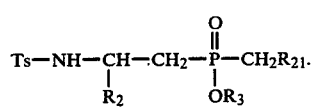

(XIII)

The intermediate of formula XIII is then treated with carbon dioxide in the presence of lithium diisopropyl amide to yield the carboxylic acid intermediate

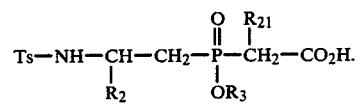

(XIV)

Removal of the remaining tolylsulfonyl protecting group such as by treatment with hydrogen bromide (48%) and reacting with the acid chloride of the formula

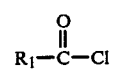

(VIII)

yields the carboxylic acid intermediate

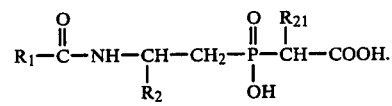

(XV)

The carboxylic acid intermediate of formula XV or an activated form thereof is then coupled with the imino or amino acid or ester of formula X as described above to yield the desired products of formula I.

Again, if either $R_1$ or $R_2$ is amino substituted lower alkyl then the amino group will be protected as described above as will the hydroxyl, amino, imidazolyl, mercaptan or guanidinyl function of $R_5$. Also, if $R_2$ is protected amino lower alkyl, then the amine of formula XIV will be deprotected by treatment with bromotrimethylsilane in methylene chloride followed by reaction with sodium in liquid ammonia or sodium naphthylide so as to avoid removal of the $R_2$ amine protecting group.

The compounds of formula I wherein A is

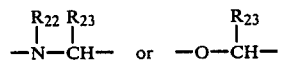

may be prepared according to the following procedure. The protected amine of formula XI is reacted with diethyl phosphate sodium salt, i.e.,

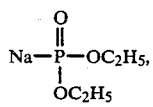

to yield the intermediate of the formula

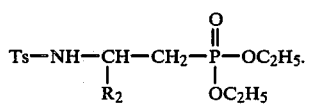 (XVI)

Treatment with hydrogen bromide (48%) in the presence of phenol and heat yields the aminophosphonic acid of the formula

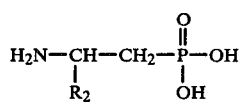 (XVII)

The aminophosphonic acid of formula XVII is then reacted with benzyloxycarbonylchloride or phthalic anhydride to yield

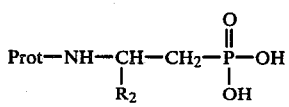 (XVIII)

wherein Prot is benzyloxycarbonyl or phthalidyl. The acid of formula XVIII is then converted to the phosphinic acid ester chloride of the formula

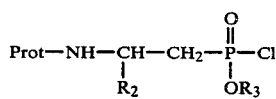 (XIX)

wherein $R_3$ is lower alkyl, benzyl or benzhydryl by treating XVIII with ethyl orthoformate, benzyl bromide, etc., followed by treatment with thionyl chloride.

The acid chloride of formula XIX is then coupled with the peptide or imino or amino acid or ester of the formula

 (XX)

wherein A is

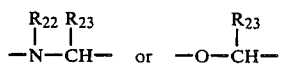

and X, $R_{22}$, and $R_{23}$ are as defined above to yield the intermediate of the formula

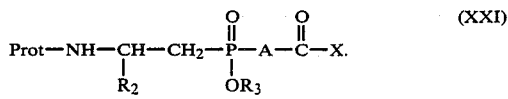 (XXI)

Removal of the protecting group such as by hydrogenation where Prot is benzyloxycarbonyl or by treatment with hydrazine where Prot is phthalidyl followed by reaction with the acid chloride of the formula

 (VIII)

yields the desired products of formula I.

Again, in preparing these compounds if either $R_1$ or $R_2$ is amino substituted lower alkyl then the amino group will be protected as described above and the amine of formula XVI will be deprotected by treatment with bromotrimethylsilane in methylene chloride followed by reaction with sodium in liquid ammonia or sodium naphthylide so as to avoid removal of the $R_2$ amine protecting group. Also, in these reactions the hydroxyl, amino, imidazolyl, mercaptan or guanidinyl function of $R_5$ will be protected as described above. Similarly, if $R_{23}$ is amino substituted lower alkyl such amino group will be protected by benzyloxycarbonyl until completion of the reaction sequences and if $R_{23}$ contains a hydroxyl, amino, imidazolyl, mercaptan, or guanidinyl group such function will be protected as described above for $R_5$.

The products of formula I wherein either or both of $R_3$ and $R_6$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_3$ and $R_6$ are hydrogen.

The ester products of formula I wherein $R_6$ is

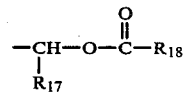

may be obtained by employing the imino or amino acid or peptide of formula X or XX in the above reactions with the ester group already in place. Such ester reactants can be prepared by treating peptide, imino, or amino acids with an acid chloride such as

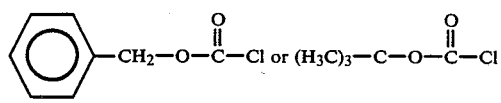

so as to protect the N-atom. The protected acid compound is then reacted in the presence of a base with a compound of the formula

 (XXIII)

wherein L is a leaving group such as chlorine, bromine, tolylsulfonyloxy, etc., followed by removal of the N-protecting group such as by treatment with acid or hydrogenation.

The ester products of formula I wherein $R_6$ is

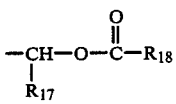

can also be obtained by treating the product of formula I wherein $R_6$ is hydrogen with a molar equivalent of the compound of formula XXIII. The diester products wherein $R_3$ and $R_6$ are the same and are

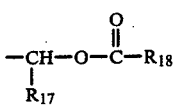

can be obtained by treating the product of formula I wherein $R_3$ and $R_6$ are both hydrogen or an alkali metal salt with two or more equivalents of the compound of formula XXIII.

The ester products of formula I wherein $R_3$ is

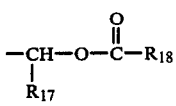

can be obtained by treating the product of formula I wherein $R_3$ is hydrogen or an alkali metal salt and $R_6$ is benzyl or benzhydryl with the compound of formula XXIII in the presence of base. Removal of the $R_6$ ester group such as by hydrogenation yields the products of formula I wherein $R_3$ is

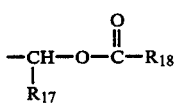

and $R_6$ is hydrogen.

The products of formula I wherein $R_7$ is amino may be obtained by reducing the corresponding products of formula I wherein $R_7$ is azido.

The preparation of the dichlorophosphine starting materials of formula III can be found in various literature references. Note, for example, Proskurnina et al., Dokl. Akad. Nauk SSSR, Vol. 159, page 619 (1964) and Issleib et al., Chem.Ber., Vol. 100, p. 3331 (1967).

The sulfonamide starting materials of formula XI can be prepared by reacting an amino alcohol of the formula

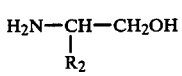

with p-toluenesulfonylchloride in pyridine. The amino alcohols of formula XXIV are, for the most part, commercially available, or can be made by treating the readily available amino acid ester of the formula

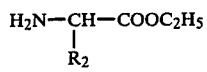

with sodium borohydrode in aqueous ethanol with heat according to the procedure of Seki et al., Chem. Pharm. Bull., Vol. 13, p. 995(1965).

The sodium phosphinate reactants of formula XII can be prepared by treating the corresponding phosphinate of the formula

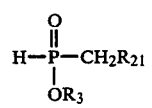

with sodium hydride in tetrahydrofuran. There are several methods in the literature for preparing the phosphinates of formula XXVI and they are reviewed by Kosolapoff et al. in "Organic Phosphorus Compounds", Vol. 4, Chapter 10, at pages 265-277.

The various imino and amino acids and esters and peptides of formulas X and XX are described in the literature and U.S. patent applications referred to above. Various substituted prolines are also disclosed by Mauger et al., Chem. Review, Vol. 66, p. 47-86 (1966). When the amino or imino acid is known, it can be readily converted to the ester by conventional means. For example, the esters where $R_6$ is t-butyl can be obtained by treating the corresponding N-carbobenzyloxyimino acid with isobutylene under acidic conditions and then removing the N-carbobenzyloxy protecting group by catalytic hydrogenation and the esters wherein $R_6$ is benzyl can be obtained by treating the imino acid with benzyl alcohol and thionyl chloride.

As disclosed by Krapcho in U.S. Ser. No. 164,985, now U.S. Pat. No. 4,316,905, the unsubstituted prolines wherein $R_7$ is

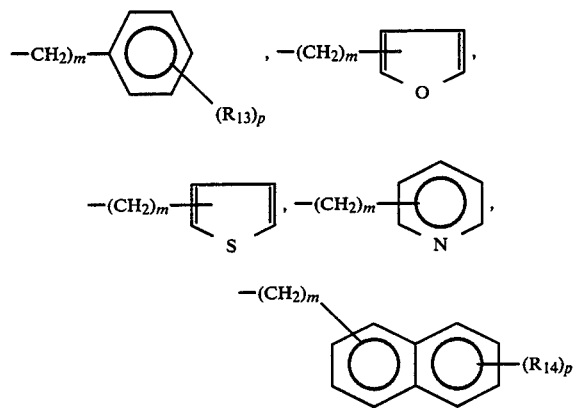

or —$(CH_2)_m$—cycloalkyl are prepared by reacting a 4-keto proline of the formula

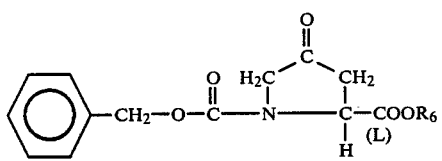

with a solution of the Grignard or lithium reagent $$R_7\text{—Mg—halo or } R_7\text{—Li} \qquad (XXVIII)$$

wherein $R_7$ is as defined above and halo is Br or Cl to yield

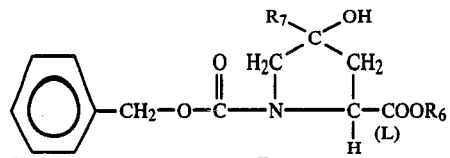 (XXIX)

This compound is treated with a dehydrating agent such as p-toluenesulfonic acid, sulfuric acid, potassium bisulfate, or trifluoroacetic acid to yield the 3,4-dehydro-4-substituted proline of the formula

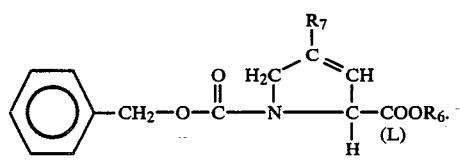 (XXX)

Removal of the N-benzyloxycarbonyl protecting group and hydrogenation of the compound of formula XXX yields the desired starting materials. The substituted proline wherein $R_7$ is cyclohexyl can be prepared by further hydrogenation of the 4-phenyl proline compound.

The substituted prolines wherein $R_7$ is the substituted amino group

may be prepared by reacting a 4-keto proline of formula XXVII with the amine

in the presence of hydrogen and catalyst or in the presence of sodium cyanotrihydridoborate.

Preferred compounds of this invention with respect to the amino or imino acid or ester part of the structure of formula I are those wherein:

$R_4$ is hydrogen.

$R_5$ is hydrogen, lower alkyl of 1 to 4 carbons,

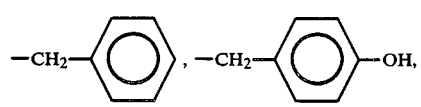

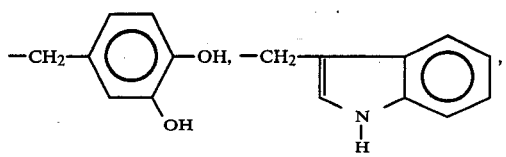

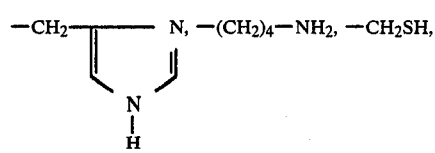

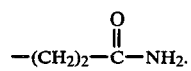

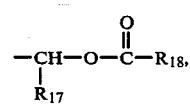

$R_6$ is hydrogen, an alkali metal salt, or $$-\underset{R_{17}}{\overset{}{CH}}-O-\overset{O}{\overset{\|}{C}}-R_{18},$$

$R_{17}$ is hydrogen or methyl and $R_{18}$ is a straight or branched chain lower alkyl of 1 to 4 carbons or phenyl.

$R_7$ is hydrogen.

$R_7$ is hydroxy.

$R_7$ is chloro or fluoro.

$R_7$ is lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

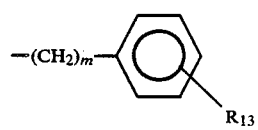

wherein m is zero, one or two, $R_{13}$ is hydrogen, methyl, methoxy, methylthio, chloro, bromo, fluoro, or hydroxy.

$R_7$ is

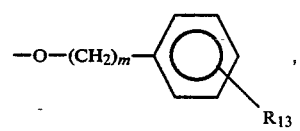

1-naphthyloxy or 2-naphthyloxy wherein m is zero, one or two, and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

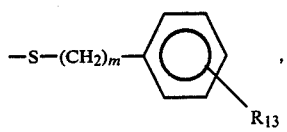

1-naphthylthio, or 2-naphthylthio wherein m is zero, one or two, and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

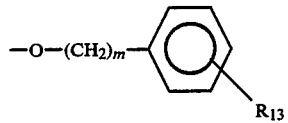

wherein m is zero, one or two, and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

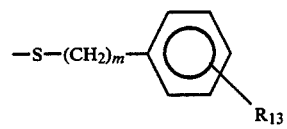

wherein m is zero, one or two, and $R_{13}$ is hydrogen, methyl, methoxy, methylthio, chloro, bromo, fluoro, or hydroxy.

$R_9$ is phenyl, 2-hydroxyphenyl, or 4-hydroxyphenyl.
$R_{10}$ are both fluoro or chloro.
$R_{10}$ are both —Y—$R_{16}$ wherein Y is O or S, $R_{16}$ is straight or branched chain alkyl of 1 to 4 carbons or the $R_{16}$ groups join to complete an unsubstituted 5- or 6-membered ring or said ring in which one or more of the carbons has a methyl or dimethyl substituent.

$R_{11}$, $R'_{11}$, $R_{12}$ and $R'_{12}$ are all hydrogen, or $R_{11}$ is phenyl, 2-hydroxyphenyl or 4-hydroxyphenyl and $R'_{11}$, $R_{12}$ and $R'_{12}$ are hydrogen.

Most preferred compounds of this invention with respect to the amino or imino acid or ester part of the structure of formula I are those wherein:

X is

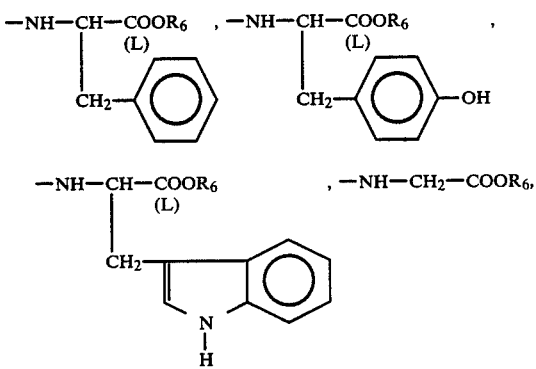

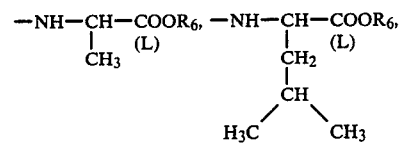

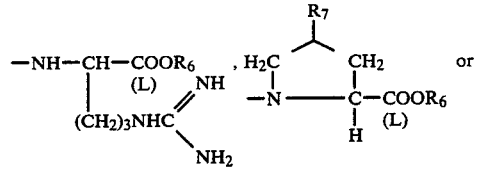

$R_6$ is hydrogen,

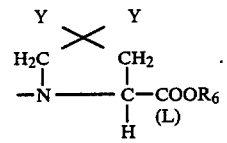

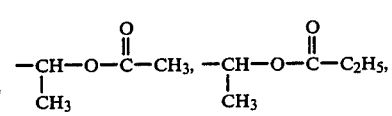

or an alkali metal salt.
$R_7$ is hydrogen.
$R_7$ is cyclohexyl.
$R_7$ is lower alkoxy of 1 to 4 carbons.
$R_7$ is

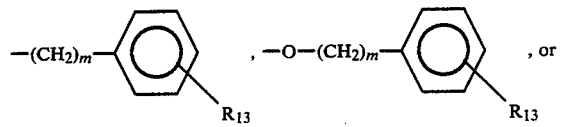

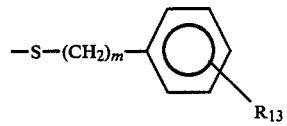

wherein m is zero, one, or two and $R_{13}$ is hydrogen, methyl, methoxy, methylthio, Cl, Br, F or hydroxy.

Y is oxygen or sulfur and t is two or three, especially wherein Y is sulfur and t is two.

Preferred compounds of this invention with respect to the phosphorus containing sidechain are those wherein:

A is —CH$_2$— or

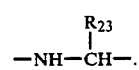

$R_1$ is lower alkyl of 1 to 4 carbons or

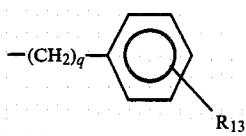

and $R_2$ is hydrogen, lower alkyl of 1 to 4 carbons, or

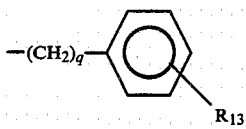

wherein q is zero or an integer from 1 to 4 and $R_{13}$ is hydrogen, methyl, methoxy, methylthio, chloro, bromo, fluoro, or hydroxy, especially wherein $R_1$ is phenyl and $R_2$ is phenylmethyl or phenylethyl.

$R_3$ is hydrogen, an alkali metal salt, lower alkyl of 1 to 4 carbons, benzyl, or

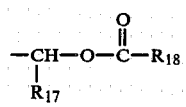

wherein $R_{17}$ is hydrogen or methyl and $R_{18}$ is straight or branched chain lower alkyl of 1 to 4 carbons or phenyl, especially hydrogen, alkali metal salt, ethyl,

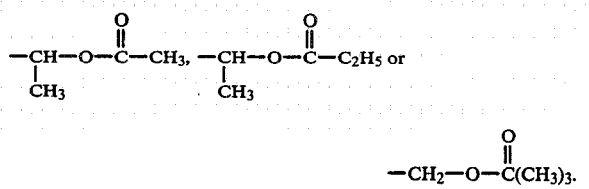

$R_{23}$ is lower alkyl of 1 to 4 carbons or amino substituted lower alkyl of 1 to 4 carbons, especially methyl or $-(CH_2)_4NH_2$.

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

As shown above, the amino or imino acid or ester portion of the molecule of the products of formula I represented by X is in the L-configuration. Depending upon the definition of $R_2$, $R_{21}$, and $R_{23}$ other asymmetric centers may be present in the phosphorus containing sidechain. Thus some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cistrans isomerism. The configuration of the final product will depend upon the configuration of the $R_7$, $R_8$ and $R_9$ substituted in the starting material of formula X or XX.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in serveral forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene divinylbenzene sulfonic acid cation exchange resin. HP-20 refers to a porous crosslinked polystyrene-divinyl benzene polymer resin.

EXAMPLE 1

(S)-1-[[[2-(Benzoylamino)-3-phenylpropyl]hydroxyphosphinyl]acetyl]-L-proline, dilithium salt (a) Methylphosphinic acid, ethyl ester To a solution of dichloromethylphosphine (18 ml., 0.2 mole) in dry ether (200 ml.) at 0° (ice bath) under argon was added dropwise a solution of triethylamine (27.8 ml., 0.2 mole) and absolute ethanol (25 ml., 0.43 mole) in dry ether (75 ml.) over a period of one hour. The mixture was then stirred at room temperature for one hour, refluxed for one hour, cooled, and filtered. The ether was removed by distillation at atmospheric pressure under argon and the residue distilled under vacuum to give pure methylphosphinic acid ethyl ester as a colorless liquid; b.p. 78°-79° (20 mm of Hg.).

(b) 4-Methylbenzenesulfonic acid, (S)-2-[[(4-methylphenyl)sulfonyl]amino]-3-phenylpropyl ester L-Phenylalaninol (10 g., 66.2 mmole) and p-toluenesulfonyl chloride (30.2 g., 158.5 mmole) were dissolved in pyridine (100 ml.) and kept under refrigeration overnight. The solution was evaporated, redissolved in chloroform, washed with water, 1N hydrochloric acid and water. The solution was evaporated and on trituration with ether 24 g. of a light yellow colored solid was obtained. This material was chromatographed on silica gel using chloroform followed by chloroform: methanol (99:1) to give after trituration with ether 19.8 g. of 4-methylbenzenesulfonic acid, (S)-2-[[(4-methylphenyl)sulfonyl]amino]-3-phenylpropyl ester; m.p. 97°-98°; $[\alpha]_D^{25} = -57.4°$ (c=1, methanol); $R_f$(ethyl acetate-hexane; 1:2)=0.39.

Anal. calc'd. for $C_{23}H_{25}NO_5S_2$: C, 60.11; H, 5.48; N, 3.05; S, 13.95. Found: C, 60.01; H, 5.58; N, 3.05; S, 13.93.

(c) (S)-Methyl[2-[[(4-methylphenyl)sulfonyl]-amino]-3-phenylpropyl]phosphinic acid, ethyl ester A solution of methylphosphinic acid, ethyl ester (3.8 g., 35.2 mmole) in dry tetrahydrofuran (50 ml.) was treated with sodium hydride 50% oil dispersion (1.45 g., 30.2 mmole) and refluxed under argon for 25 minutes. The resulting clear solution was allowed to cool to room temperature, treated with (S)-4-methylbenzenesulfonic acid, 2-[[(4-methylphenyl)sulfonyl]amino]-3-phenylpropyl ester (4.59 g., 10.0 mmole), and stirred at room temperature under argon. After 10 minutes, a white solid had separated; additional tetrahydrofuran was added (50 ml.) and stirring was continued overnight. The mixture was then partitioned between ethyl acetate-5% potassium bisulfate (50 ml. each). The ethyl acetate phase was washed successively with saturated sodium bicarbonate and saturated sodium chloride, dried ($Na_2SO_4$), and evaporated. The residue was triturated with ether to give 3.55 g. of (S)-methyl-[2-[[(4-methylphenyl)sulfonyl]amino]-3-phenylpropyl]phosphinic acid, ethyl ester as white crystals. Recrystallization from ethyl acetate-hexane gives an analytical sample; m.p. 121°-122°; $[\alpha]_D^{25} = -62.4°$ (c=1.06, methanol); $R_f$(ethyl acetate)=0.25.

Anal. calc'd. for $C_{19}H_{26}NO_4PS$: C, 57.71; H, 6.63; N, 3.54. Found: C, 57.64; H, 6.60; N, 3.56.

(d) (S)-[Ethoxy[2-[[(4-methylphenyl)sulfonyl]-amino]-3-phenylpropyl]phosphinyl]acetic acid A solution of diisopropylamine (2.55 ml., 18.2 mmole) in dry tetrahydrofuran (30 ml.) at 0° (ice bath) under argon was treated via syringe with 2.4M butyllithium-hexane (6.0 ml., 14.4 mmole). After stirring for twenty minutes, the mixture was cooled to −78° (dry ice-acetone bath) and treated via motor driven syringe with a solution of (S)-methyl[2-[[(4-methylphenyl)sulfonyl]amino]-3-phenylpropyl]-phosphinic acid, ethyl ester (2.4 g., 6.08 mmole) in dry tetrahydrofuran (15 ml.) at a rate of 0.39 ml./min. The resulting mixture was stirred at −78° for an additional 45 minutes and then treated with dry carbon dioxide (passed through 5 A° molecular sieves) for 30 minutes. The mixture was then allowed to warm to room temperature, stirred for 30 minutes and partitioned between ethyl acetate-5% potassium bisulfate. The ethyl acetate layer was washed with saturated sodium chloride, dried ($Na_2SO_4$) and evaporated. The residue was filtered through a short column of silica (75 g.) eluting with acetic acid-methanol-dichloromethane (2:5:120). The crude product was taken up in saturated sodium bicarbonate and washed with ethyl acetate. The aqueous phase was acidified with concentrated hydrochloric acid (pH 1), the precipitate collected, washed with water and dried in vacuo over $P_2O_5$ to give 2.1 g. of (S)-[ethoxy[2-[[(4-methylphenyl)sulfonyl]amino]-3-phenylpropyl]phosphinyl] acetic acid as a white solid; m.p. 110°–112°; $[\alpha]_D^{25} = -47.0°$ (c=1.21, methanol), $R_f$ (10% methanol-dichloromethane)=0.22.

Anal. calc'd. for $C_{20}H_{26}NO_6PS$. 1.0 $H_2O$: C, 52.51; H, 6.17; N, 3.06; P, 6.77. Found: C, 52.25; H, 5.92; N, 2.92; P, 6.5.

(e) (S)-[(2-Amino-3-phenylpropyl)hydroxyphosphinyl]acetic acid

A mixture of (S)-[ethoxy[2-[[(4-methylphenyl)sulfonyl]amino]-3-phenylpropyl]phosphinyl]acetic acid (2.4 g., 5.47 mmole), phenol (2.4 g., 25.5 mmole), and 48% aqueous hydrobromic acid (25 ml.) was refluxed for two hours. The cooled mixture was diluted with water (50 ml.) and washed with ethyl acetate (2×25 ml.). The aqueous phase was evaporated to dryness, taken up in water (25 ml.) and evaporated again. This was repeated twice more. Finally, the pale yellow residue was taken up in water and applied to an AG 50 W-X2 (H+ form) column (50 ml. bed volume) and eluted first with water (collecting six, 50 ml. fractions) then 5% pyridine-water (collecting six, 50 ml. fractions). The fractions containing the desired product were combined and evaporated to dryness. The solid residue was triturated with acetonitrile to give 1.10 g. of (S)-[(2-amino-3-phenylpropyl)hydroxyphosphinyl]acetic acid as a white crystalline solid; m.p. 235° (dec.); $[\alpha]_D^{25} = +2.2°$ (c=1.00, 1N hydrochloric acid); $R_f$(isopropanol-conc. $NH_4OH$-water; 7:2:1)=0.37. Electrophoresis pH 6.5, 2000 V, 60 minutes, single spot +5.3 cm., visualized with carboxyl reagent or ninhydrin.

Anal. calc'd. for $C_{11}H_{16}NO_4P$: C, 51.36; H, 6.27; N, 5.45; P, 12.04. Found: C, 51.31; H, 6.28; N, 5.55; P, 12.0.

(f)
(S)-[[2-(Benzoylamino)-3-phenylpropyl]hydroxyphosphinyl]acetic acid

A suspension of (S)-[(2-amino-3-phenylpropyl)hydroxyphosphinyl]acetic acid (10 g., 3.89 mmole) in a mixture of dioxane (6 ml.) and water (3 ml.) was cooled in an ice bath and treated with triethylamine (2.0 ml., 14.5 mmole). A clear solution was obtained. The mixture was then treated with benzoyl chloride (0.55 ml., 4.74 mmole) dropwise over a 5 minute period. After stirring at 0° for one hour, the mixture was acidified (pH 1) with concentrated hydrochloric acid and most of the solvent removed in vacuo. The residue was triturated with water, the white solid filtered off and washed thoroughly with water. The solid was air-dried, triturated (three times) with ether to remove traces of benzoic acid and finally dried in vacuo over $P_2O_5$ to give 1.2 g. of (S)-[[2-(benzoylamino)-3-phenylpropyl]hydroxyphosphinyl]acetic acid; m.p. 105°-107°; $[\alpha]_D^{25} = -27.8°$ (c=1.00, methanol); $R_f$ (isopropanol-conc. $NH_4OH$-water; 7:2:1)=0.56.

Anal. calc'd. for $C_{18}H_{20}NO_5P \cdot 1.0\ H_2O$: C, 56.99; H, 5.85; N, 3.69; P, 8.16. Found: C, 56.89; H, 5.80; N, 3.95; P, 7.9.

(g)
(S)-1-[[[2-(Benzoylamino)-3-phenylpropyl]hydroxyphosphinyl]acetyl]-L-proline, phenylmethyl ester A solution of (S)-[[2-(benzylamino)-3-phenylpropyl]hydroxyphosphinyl]acetic acid (1.0 g., 2.77 mmole) in dry tetrahydrofuran (15 ml.) at 0° (ice bath) under argon was treated with carbonyldiimidazole (0.48 g., 2.96 mmole). After 50 minutes, the mixture was treated with triethylamine (1.2 ml., 8.67 mmole), and L-proline, phenylmethyl ester, hydrochloride salt (0.7 g., 2.9 mmole), allowed to warm to room temperature and stirred overnight. The reaction mixture was partitioned between ethyl acetate-5% potassium bisulfate. The ethyl acetate layer was washed successively with 5% potassium bisulfate, 5% sodium biphosphate (pH 4.5 buffer) and saturated sodium chloride, dried ($Na_2SO_4$) and evaporated. The crude product (1.24 g.) was purified by flash chromatography on silica gel (60 g.) eluting with acetic acid-methanol-dichloromethane (1:1:26) to give 1.12 g. of (S)-1-[[[2-(benzoylamino)-3-phenylpropyl]hydroxyphosphinyl]acetyl]-L-proline, phenylmethyl ester as a white foam; $R_f$(acetic acid-methanol-dichloromethane; 1:1:20)=0.29; $R_f$ (isopropanol-conc. $NH_4OH$-water)=0.76.

(h)
(S)-1-[[[2-(Benzoylamino)-3-phenylpropyl]hydroxyphosphinyl]acetyl]-L-proline, dilithium salt A solution of the ester product from part (g) (1.05 g., 1.92 mmole) in absolute methanol (60 ml.) was treated with 10% palladium-carbon catalyst (0.3 g.) and hydrogenated in a Parr apparatus at 50 psi for 2.5 hours. The mixture was filtered through Celite and evaporated to dryness. The residue (0.87 g.) was taken up in 1N lithium hydroxide (3 ml.) and water (4 ml.) and passed down an AG50W-X8 (Li+ form) column (40 ml. bed volume) eluting with water. The fractions containing the desired product were combined and lyophilized. The crude lyophilate (0.8 g.) was chromatographed on a HP-20 column (1 inch diameter column, 200 ml. bed volume) eluting with a linear gradient of water (100%) to acetonitrile (100%) at a flow rate of 5 ml./min., collecting 5 ml. fractions. Fractions number 82 to 96 were pooled, evaporated, taken up in water, filtered (millipore) and lyophilized to give 0.71 g. of (S)-1-[[[2-(benzoylamino)-3-phenylpropyl]hydroxyphosphinyl]acetyl]-L-proline, dilithium salt; $[\alpha]_D^{25} = -63.8°$ (c=1.12, methanol); $R_f$ (isopropanol-conc. $NH_4OH$-water; 7:2:1)=0.5; electrophoresis pH 6.5, 2000 V, 40 minutes, single spot +4.8 cm., visualized with carboxyl reagent.

Anal. calc'd. for $C_{23}H_{25}N_2O_6PLi_2 \cdot 1.4\ H_2O$: C, 55.75; H, 5.65; N, 5.65; P, 6.25. Found: C, 55.67; H, 5.45; N, 5.52; P, 6.3.

EXAMPLE 2
(S)-1-[[[2-(Benzoylamino)-4-methylpentyl]hydroxyphosphinyl]acetyl]-L-proline, dilithium salt

(a) 4-Methylbenzenesulfonic acid, (S)-2-[[(4-methylphenyl)sulfonyl]amino]-4-methylpentyl ester A solution of (S)-2-amino-4-methylpentanol (4.9 g., 41.8 mmole) in dry pyridine (20 ml.) at 0° (ice bath) was treated with p-toluenesulfonyl chloride (16.7 g., 87.6 mmole) in small portions over a 15 minute period. After 4 hours, the mixture was partitioned between ethyl acetate- 1N hydrochloric acid (100 ml. each). The ethyl acetate layer was washed successively with 1N hydrochloric acid, saturated sodium bicarbonate, and saturated sodium chloride, dried ($Na_2SO_4$), and evaporated. The orange residue was filtered through a pad of silica gel (75 g.) eluting with dichloromethane. Evaporation of the dichloromethane and trituration of the residue with diisopropyl ether-ethyl ether gave 14 g. of 4-methylbenzenesulfonic acid, (S)-2-[[(4-methylphenyl)sulfonyl]amino]-4-methylpentyl ester as white crystals; m.p. 99°-101°. Recrystallization from cyclohexane gave an analytical sample; m.p. 99°-101.5°; $[\alpha]_D^{25} = -53.2$ (c=1.00, methanol); $R_f$ (ethyl acetate/hexane; 1:2)=0.43.

Anal. calc'd. for $C_{20}H_{27}NO_5S_2$: C, 56.45; H, 6.39; N, 3.29; S, 15.07. Found: C, 56.43; H, 6.64; N 3.25; S, 15.06.

(b)
(S)-Methyl[2-[[(4-methylphenyl)sulfonyl]amino]-4-methylpentyl]phosphinic acid, ethyl ester A solution of methylphosphinic acid, ethyl ester (3.24 g., 30 mmole) in dry tetrahydrofuran (100 ml.) was treated with sodium hydride 50% oil dispersion (1.4 g., 30.0 mmole) and refluxed under argon for 1.5 hours. The resulting clear solution was allowed to cool to room temperature, treated with (S)-4-methylbenzenesulfonic acid, 2-[[(4-methylphenyl)sulfonyl]amino]-4-methylpentyl ester (4.25 g., 10.0 mmole), and stirred at room temperature. After two hours, the mixture was partitioned between ethyl acetate-5% potassium bisulfate (50 ml. each). The ethyl acetate phase was washed successively with saturated sodium bicarbonate and saturated sodium chloride, dried ($MgSO_4$), and evaporated. The residue was triturated with hexane to give 3.2 g. of (S)-methyl [2-[[(4-methylphenyl)sulfonyl]amino]-4-methylpentyl]phosphinic acid, ethyl ester as an off white solid; m.p. 96°-105°. Tlc (5% methanol/dichloromethane) showed two spots (~3:2), $R_f$=0.47, 0.55 (isomers at phosphorus); $[\alpha]_D^{25} = -30.9°$ (c=1.00, methanol).

(c)
(S)-[(2-Amino-4-methylpentyl)hydroxyphosphinyl]acetic acid

A solution of diisopropylamine (6.5 ml., 46.5 mmole) in dry pentane (100 ml.) at 0° (ice bath) under argon was treated via syringe with 1.6M butyllithium-hexane (12 ml., 19.2 mmole). After stirring at 0° for 10 minutes, the mixture was evaporated to dryness (0.5 mm of Hg.). The white solid residue was taken up in dry tetrahydrofuran (50 ml.) and cooled to −78° (dry ice-water bath) and treated via motor driven syringe with a solution of (S)-methyl[2-[[(4-methylphenyl)sulfonyl]amino]-4-methylpentyl]phosphinic acid, ethyl ester (2.9 g., 8.02 mmole) in dry tetrahydrofuran (15 ml.) at a rate of 1.0 ml./min. The resulting mixture was stirred at −78° for an additional 20 minutes and then treated with dry carbon dioxide (passed through 5 A° molecular sieves) for 20 minutes. The mixture was then allowed to warm to room temperature, stirred for 30 minutes and evaporated. The residue was taken up in saturated sodium bicarbonate, washed with ethyl acetate, acidified with concentrated hydrochloric acid and thoroughly extracted with dichloromethane. The combined dichloromethane extracts were dried (MgSO$_4$) and evaporated to give 2.7 g. of crude monoacid as a white foam. R$_f$ (acetic acid/methanol/dichloromethane, 1:1:20)=0.30.

A mixture of the crude monoacid (2.7 g., 6.67 mmole), phenol (2.7 g., 28.7 mmole) and 48% aqueous hydrobromic acid (35 ml.) was refluxed for 3.5 hours. The cooled mixture was diluted with water (40 ml.) and washed with dichloromethane (4×50 ml.). The aqueous phase was evaporated to dryness, taken up in water (30 ml.) and evaporated again. This was repeated twice more. Finally, the orange residue was taken up in water and applied to an AG 50 W-X2 (H$^+$ form) column (70 ml. bed volume) and eluted first with water then 10% pyridine-water. The fractions containing the desired product were combined and evaporated to dryness. The solid residue was triturated with acetonitrile to give 1.10 g. of (S)-[(2-amino-4-methylpentyl)hydroxyphosphinyl]acetic acid as a tan crystalline solid; m.p. 225° (dec.); R$_f$ (isopropanol/conc. NH$_4$OH/water; 7:2:1)=0.10; $[\alpha]_D^{25}$=+9.9° (c=1.00, 1N hydrochloric acid).

Anal. calc'd. for C$_8$H$_{18}$NO$_4$P: C, 42.90; H, 8.10; N, 6.25. Found: C, 43.08; H, 8.11; N, 6.23.

(d)
(S)-[[2-(Benzoylamino)-4-methylpentyl]hydroxyphosphinyl]acetic acid

A suspension of (S)-[(2-amino-4-methylpentyl)hydroxyphosphinyl]acetic acid (1.0 g., 4.46 mmole) in acetonitrile (100 ml.) was treated with bistrimethylsilyl acetamide (4.4 ml., 17.8 mmole). After 20 minutes a clear solution was obtained. After an additional 20 minutes, the mixture was treated with benzoyl chloride (1.0 g., 7.11 mmole). After 5 hours at room temperature, the mixture was partitioned between 5% sodium bicarbonate-ether. The aqueous phase was acidified with concentrated hydrochloric acid (pH 1) and extracted with ethyl acetate. The ethyl acetate extract was washed with saturated sodium chloride, dried (MgSO$_4$), and evaporated. The residue (17 g.) was dissolved in 1N lithium hydroxide (6 ml.) and chromatographed on a HP-20 column (1 inch diameter, 200 ml. bed volume) eluting with a linear gradient of water-acetonitrile (0→90%) at a flow rate of 5 ml./min., collecting 5 ml. fractions. The fractions containing the desired product (Tlc) were combined, evaporated, and the residue partitioned between ethyl acetate-1N hydrochloric acid. The ethyl acetate layer was washed with saturated sodium chloride, dried (MgSO$_4$) and evaporated to give 0.9 g. of (S)-[[2-(benzoylamino)-4-methylpentyl]hydroxyphosphinyl]acetic acid as a white foam. R$_f$ (isopropanol/conc. NH$_4$OH/water; 7:2:1)=0.70; $[\alpha]_D^{25}$=−4.0 (c=0.50, methanol).

(e)
(S)-1-[[[2-(Benzoylamino)-4-methylpentyl]hydroxyphosphinyl]acetyl]-L-proline, phenylmethyl ester A solution of (S)-[[2-(benzoylamino)-4-methylpentyl]hydroxyphosphinyl]acetic acid (0.85 g., 2.60 mmole) in dry tetrahydrofuran (10 ml.) at 0° (ice bath) under argon was treated with carbonyldiimidazole (0.50 g., 3.08 mmole). After one hour, the mixture was treated with triethylamine (1.0 ml., 7.23 mmole), and L-proline, phenylmethyl ester, hydrochloride salt (0.75 g., 3.1 mmole), allowed to warm to room temperature and stirred overnight. The reaction mixture was partitioned between ethyl acetate-5% potassium bisulfate. The ethyl acetate layer was washed successively with 5% potassium bisulfate, 5% sodium biphosphate (pH 4.5 buffer) and saturated sodium chloride, dried (MgSO$_4$) and evaporated. The residue (1.3 g.) was taken up in 1N lithium hydroxide (2.5 ml.), diluted with saturated sodium bicarbonate (30 ml.) and washed with ether (twice). The aqueous phase was acidified with concentrated hydrochloric acid (pH 1) and extracted with ethyl acetate. The combined ethyl acetate extracts were washed with saturated sodium chloride, dried (MgSO$_4$) and evaporated to give 0.9 g. of (S)-1-[[[2-(benzoylamino-4-methylpentyl]hydroxyphosphinyl]acetyl]-L-proline, phenylmethyl ester as a white foam. R$_f$ (acetic acid/methanol/dichloromethane; 1:1:20)=0.25; R$_f$ (isopropanol/conc. NH$_4$OH/water; 7:2:1)=0.74.

(f)
(S)-1-[[[2-(Benzoylamino)-4-methylpentyl]hydroxyphosphinyl]acetyl]-L-proline, dilithium salt A solution of the ester product from part (e) (0.9 g.) in absolute methanol (50 ml.) was treated with 10% palladium-carbon catalyst (0.2 g.) and hydrogenated in a Parr apparatus at 50 psi for 1.5 hours. The mixture was filtered through Celite and evaporated to dryness. The residue (0.70 g.) was taken up in 1N lithium hydroxide (5.25 ml.) and was chromatographed on a HP-20 column (1 inch diameter, 200 ml. bed volume) eluting with a linear gradient of water-acetonitrile (0→90%) at a flow rate of 5 ml./min., collecting 5 ml. fractions. The fractions containing the desired product were pooled, evaporated, taken up in water, millipore filtered, and lyophilized to give 0.55 g. of (S)-1-[[[2-(benzoylamino)-4-methylpentyl]hydroxyphosphinyl]acetyl]-L-proline, dilithium salt; R$_f$ (isopropanol/conc. NH$_4$OH/water; 7:2:1)=0.60.

EXAMPLE 3
1-[[[2-(Benzoylamino)-4-phenylbutyl]hydroxyphosphinyl]acetyl]-L-proline, dilithium salt (a) 4-Methylbenzenesulfonic acid, 2-[[(4-methylphenyl)sulfonyl]amino]-4-phenylbutyl ester A suspension of d,l-homophenylalanine (5 g., 27.9 mmole) in absolute ethanol (60 ml.) was cooled to 0°

(ice bath) and saturated with hydrochloric acid gas. The mixture was allowed to warm to room temperature and stirred overnight. A stream of nitrogen was then passed through the solution to remove the bulk of the hydrochloric acid and the mixture was evaporated to dryness. The solid residue was triturated with ether, filtered and dried to give ($\pm$)-$\alpha$-aminobenzenebutanoic acid, ethyl ester, monohydrochloride as a fluffy white solid; m.p. 129°–130°. $R_f$ (acetic acid/methanol/dichloromethane; 1:1:8)=0.63.

To a solution of sodium borohydride (4.5 g., 0.119 mole) in 50% aqueous ethanol (60 ml.) was added dropwise a solution of ($\pm$)-$\alpha$-aminobenzenebutanoic acid, ethyl ester, monohydrochloride (6.2 g., 25.4 mmole) in 50% aqueous ethanol (60 ml.) at room temperature. After the addition was complete, the mixture was refluxed for 5 hours and then allowed to stand at room temperature overnight. The ethanol and most of the water were evaporated off and the residue was partitioned between ethyl acetate-water (75 ml. each). The organic phase was separated and the aqueous phase was reextracted with ethyl acetate. The combined extracts were washed with saturated sodium chloride, dried ($Na_2SO_4$), and evaporated to give 3.6 g. of crude amino alcohol as a colorless oil. $R_f$ (acetic acid/methanol/dichloromethane; 1:1:8)=0.41.

The crude amino alcohol (3.6 g., 21.8 mmole) was taken up in dry pyridine (20 ml.), cooled in an ice bath under argon, and treated with p-toluenesulfonyl chloride (8.4 g., 44 mmole) in small portions over a 15 minute period. The mixture was allowed to slowly warm to room temperature. After 5 hours, the mixture was partitioned between ethyl acetate-1N hydrochloric acid. The ethyl acetate phase was washed successively with 1N hydrochloric acid, saturated sodium bicarbonate, and saturated sodium chloride, dried ($Na_2SO_4$), and evaporated. The orange residue was filtered through a pad of silica gel (50 g.) eluting with dichloromethane. Evaporation of the dichloromethane and trituration of the residue with diisopropylether gave 8.05 g. of 4-methylbenzenesulfonic acid, 2-[[(4-methylphenyl)sulfonyl]amino]-4-phneylbutyl ester; m.p. 94°–96°. An analytical sample recrystallized from ethyl acetate-hexane had a m.p. 95°–97°; $R_f$ (ethyl acetate/hexane; 1:2)=0.28.

Anal. calc'd. for $C_{24}H_{27}NO_5S_2$: C, 60.86; H, 5.75; N, 2.96; S, 13.54. Found: C, 60.84; H, 5.68; N, 2.90; S, 13.30.

(b)
Methyl[2-[[(4-methylphenyl)sulfonyl]amino]-4-phenylbutyl]phosphinic acid, ethyl ester A solution of methylphosphinic acid, ethyl ester (3.8 g., 35.2 mmole) in dry tetrahydrofuran (50 ml.) was treated with sodium hydride 50% oil dispersion (1.45 g., 30.2 mmole) and refluxed under argon for 20 minutes. The resulting clear solution was allowed to cool to room temperature, treated with 4-methylbenzenesulfonic acid, 2-[[(4-methylphenyl)sulfonyl]amino]-4-phenylbutyl ester (4.75 g., 10 mmole) and stirred at room temperature under argon. After 15 minutes, a white solid had separated; additional tetrahydrofuran was added (50 ml.) and stirring was continued overnight. The mixture was then partitioned between ethyl acetate-5% potassium bisulfate (50 ml. each). The ethyl acetate phase was washed successively with saturated sodium bicarbonate and saturated sodium chloride, dried ($Na_2SO_4$), and evaporated. The residue was triturated with diisopropyl ether to give 3.9 g. of methyl[2-[[(4-methylphenyl)sulfonyl]amino]-4-phenylbutyl]phosphinic acid, ethyl ester as white crystals; m.p. 107°–108°. Recrystallization from ethyl acetate gave an analytical sample; m.p. 108°–109°; $R_f$(ethyl acetate)=0.18.

Anal. calc'd. for $C_{20}H_{28}NO_4PS$: C, 58.66; H, 6.89; N, 3.42; P, 7.56; S, 7.83. Found: C, 58.36; H, 6.81; N, 3.34; P, 7.3; S, 7.57.

(c) [(2-Amino-4-phenylbutyl)hydroxyphosphinyl]acetic acid

A solution of diisopropylamine (3.40 ml., 24.3 mmole) in dry tetrahydrofuran (40 ml.) at 0° (ice bath) under argon was treated via syringe with 1.6M butyllithiumhexane (12.0 ml., 19.2 mmole). After stirring at 0° for twenty minutes, the mixture was cooled to −78° (dry ice-water bath) and treated via motor driven syringe with a solution of methyl[2-[[(4-methylphenyl)sulfonyl]amino]-4-phenylbutyl]phosphinic acid, ethyl ester (3.30 g., 8.07 mmole) in dry tetrahydrofuran (20 ml.) at a rate of 0.48 ml./min. The resulting mixture was stirred at −78° for an additional 45 minutes and then treated with dry carbon dioxide (passed through 5 A° molecular sieves) for 30 minutes. The mixture was then allowed to warm to room temperature, stirred for 30 minutes and partitioned between ethyl acetate-5% potassium bisulfate. The ethyl acetate layer was washed with saturated sodium chloride, dried ($Na_2SO_4$) and evaporated. The residue was taken up in saturated sodium bicarbonate, washed with ethyl acetate (twice), acidified with concentrated hydrochloric acid (pH 1.0) and thoroughly extracted with dichloromethane. The combined dichloromethane extracts were dried ($Na_2SO_4$) and evaporated to give 3.45 g. of crude monoacid as a white foam. $R_f$(10% methanol/dichloromethane)=0.15.

A mixture of the crude monoacid (3.45 g., 7.62 mmole), phenol (3.7 g., 39.4 mmole), and 48% aqueous hydrobromic acid (35 ml.) was refluxed for 2.5 hours. The cooled mixture was diluted with water (70 ml.) and washed with ethyl acetate (2×25 ml.). The aqueous phase was evaporated to dryness, taken up in water (30 ml.) and evaporated again. This was repeated twice more. Finally, the pale yellow residue was taken up in water and applied to an AG 50 W-X2 (H+ form) column (40 ml. bed volume) and eluted first with water then 5% pyridine-water. The fractions containing the desired product were combined and evaporated to dryness. The solid residue was triturated with acetonitrile to give 1.50 g. of [(2-amino-4-phenylbutyl)hydroxyphosphinyl]acetic acid as a white crystalline solid; m.p. 214° (dec.); $R_f$ (isopropanol/conc. $NH_4OH$/water; 7:2:1)=0.40.

Anal. calc'd. for $C_{12}H_{18}NO_4P$: C, 53.13; H, 6.69; N, 5.16; P, 11.42. Found: C, 52.99; H, 6.40; N, 5.12; P, 11.4.

(d)
[[2-(Benzoylamino)-4-phenylbutyl]hydroxyphosphinyl]acetic acid, dilithium salt A suspension of [(2-amino-4-phenylbutyl)hydroxyphosphinyl]acetic acid (1.0 g., 3.69 mmole) in a mixture of dioxane (6 ml.) and water (3 ml.) was cooled in an ice bath and treated with triethylamine (2.0 ml., 14.5 mmole). A clear solution was obtained. The mixture was then treated with benzoyl chloride (0.65 ml., 5.60 mmole) dropwise over a 5 minute period. After stirring at 0° for two hours, the mixture was acidified (pH 1) with concentrated hydrochloric acid and most of the solvent removed in vacuo. The residue was partitioned between ethyl acetate-water, the ethyl acetate layer was washed with saturated sodium chloride, dried (Na$_2$SO$_4$), and evaporated. The residue was taken up in 1N lithium hydroxide (5 ml., 5 mmole) and passed down an AG50 W-X8 (Li+ form) column (40 ml. bed volume) eluting with water. The product containing fractions were combined and evaporated. The crude product was chromatographed on a HP-20 column (1 inch diameter column, 200 ml. bed volume) eluting with a linear gradient of water-acetonitrile (0–100%) at a flow rate of 5 ml./min., collecting 5 ml. fractions. The fractions containing the desired product (Tlc) were combined, evaporated, taken up in water, millipore filtered, and lyophilized to give 0.95 g. of [[2-(benzoylamino)-4-phenylbutyl]hydroxyphosphinyl]acetic acid, dilithium salt as a white solid. $R_f$ (isopropanol/conc. NH$_4$OH/water; 7:2:1)=0.53.

Anal. calc'd. for C$_{19}$H$_{20}$NO$_5$PLi$_2$.H$_2$O: C, 56.31; H, 5.47; N, 3.46; P, 7.64. Found: C, 56.13; H, 5.33; N, 3.45; P, 7.8.

(e)
1-[[[2-(Benzoylamino)-4-phenylbutyl]hydroxyphosphinyl]acetyl]-L-proline, phenylmethyl ester The dilithium salt product from part (d) (0.85 g., 2.2 mmole) was partitioned between dichloromethane-1N hydrochloric acid (50 ml. each). The aqueous phase was reextracted with methylene chloride (50 ml.) and the combined extracts were dried (Na$_2$SO$_4$) and evaporated. The residue (0.82 g.) was taken up in dry tetrahydrofuran (15 ml.), cooled to 0° (ice bath) under argon, and treated with carbonyldiimidazole (0.4 g., 2.47 mmole). After one hour, the mixture was treated with triethylamine (1.1 ml., 7.95 mmole), and L-proline, phenylmethyl ester, hydrochloride salt (0.65 g., 2.69 mmole), allowed to warm to room temperature and stirred overnight. The reaction mixture was then partitioned between ethyl acetate-5% potassium bisulfate. The ethyl acetate layer was washed successively with 5% potassium bisulfate, 5% sodium biphosphate (pH 4.5 buffer) and saturated sodium chloride, dried (Na$_2$SO$_4$) and evaporated. The crude product (1.14 g.) was purified by flash chromatography on silica gel (55 g.) eluting with acetic acid-methanol-dichloromethane (1:1:26) to give 0.9 g. of 1-[[[2-(benzoylamino)-4-phenylbutyl]hydroxyphosphinyl]acetyl]-L-proline, phenylmethyl ester as a white foam. $R_f$ (acetic acid/methanol/dichloromethane; 1:1:20)=0.19. $R_f$ (isopropanol/conc. NH$_4$OH/water; 7:2:1)=0.76.

(f)
1-[[[2-(Benzoylamino)-4-phenylbutyl]hydroxyphosphinyl]acetyl]-L-proline, dilithium salt A solution of the ester product from part (e) in absolute methanol (60 ml.) is treated with 10% palladium-carbon catalyst (0.3 g.) and hydrogenated in a Parr apparatus at 50 psi for 2.5 hours. The mixture is filtered through Celite and evaporated to dryness. The residue is taken up in 1N lithium hydroxide (3 ml.) and water (4 ml.) and passed down an AG50W-X8 (Li+ form) column (40 ml. bed volume) eluting with water. The fractions containing the desired product are combined and lyophilized. The crude lyophilate is chromatographed on a HP-20 column (1 inch diameter column, 200 ml. bed volume) eluting with a linear gradient of water (100%) to acetonitrile (100%) at a flow rate of 5 ml./min., collecting 5 ml. fractions. The fractions containing the desired product are pooled, evaporated, taken up in water, millipore filtered and lyophilized to give 1-[[[2-(benzoylamino)-4-phenylbutyl]hydroxyphosphinyl]acetyl]-L-proline, dilithium salt.

EXAMPLE 4

1-[[[2-(Benzoylamino)ethyl]hydroxyphosphinyl]acetyl]-L-proline, dilithium salt (a) 4-Methylbenzenesulfonic acid, 2-[[(4-methylphenyl)sulfonyl]amino]ethyl ester A solution of 2-aminoethanol (3.05 g., 49 mmole) in dry pyridine (20 ml.) at 0° (ice bath) was treated with p-toluenesulfonyl chloride (20 g., 105 mmole) in small portions over a 15 minute period. The mixture was allowed to slowly warm to room temperature. After 3 hours, the mixture was partitioned between ethyl acetate-1N hydrochloric acid (100 ml. each). The ethyl acetate layer was washed successively with 1N hydrochloric acid, saturated sodium bicarbonate, and saturated sodium chloride, dried (Na$_2$SO$_4$), and evaporated. The orange residue was filtered through a pad of silica gel (75 g.) eluting with dichloromethane. Evaporation of the dichloromethane and trituration of the residue with ether gave 15.8 g. of 4-methylbenzenesulfonic acid, 2-[[(4-methylphenyl)sulfonyl]amino]ethyl ester as white crystals; m.p. 89°–90°; $R_f$ (ethyl acetate/hexane; 1:2)=0.27. A sample recrystallized from diisopropyl ether had a m.p. of 89°–90°.

(b)
Methyl[2-[[(4-methylphenyl)sulfonyl]amino]ethyl]phosphinic acid, ethyl ester A solution of methylphosphinic acid, ethyl ester (3.8 g., 35.2 mmole) in dry tetrahydrofuran (50 ml.) was treated with sodium hydride 50% oil dispersion (1.45 g., 30.2 mmole) and refluxed under argon for 25 minutes. The resulting clear solution was allowed to cool to room temperature, treated with 4-methylbenzenesulfonic acid, 2-[[(4-methylphenyl)sulfonyl]amino]ethyl ester (3.7 g., 10.0 mmole), and stirred at room temperature under argon. After 5 hours, the mixture was partitioned between ethyl acetate-5% potassium bisulfate (50 ml. each). The ethyl acetate phase was washed successively with saturated sodium bicarbonate and saturated sodium chloride, dried (Na$_2$SO$_4$), and evaporated. The residue was triturated with diisopropyl ether to give 2.56 g. of methyl[2-[[(4-methylphenyl)sulfonyl]amino]ethyl]phosphinic acid, ethyl ester as white crystals; m.p. 124°–126°; $R_f$(10% methanol/dichloromethane)=0.54. A sample recrystallized from ethyl acetate-hexane had a m.p. 126°–127°.

(c) [(2-Aminoethyl)hydroxyphosphinyl]acetic acid

A solution of diisopropylamine (3.4 ml., 24.3 mmole) in dry tetrahydrofuran (40 ml.) at 0° (ice bath) under argon was treated via syringe with 1.6M butyllithium-hexane (12 ml., 19.2 mmole). After stirring at 0° for twenty minutes, the mixture was cooled to −78° (dry ice-acetone bath) and treated via motor driven syringe with a solution of methyl[2-[[(4-methylphenyl)sulfonyl]amino]ethyl]phosphinic acid, ethyl ester (2.44 g., 8.0 mmole) in dry tetrahydrofuran (55 ml.) at a rate of 1.5 ml./min. The resulting mixture was stirred at −78° for an additional 45 minutes and then treated with dry carbon dioxide (passed through 5 A° molecular sieves) for 30 minutes. The mixture was then allowed to warm to room temperature, stirred for 30 minutes and partitioned between ethyl acetate-1N hydrochloric acid (100 ml. each). The aqueous phase was reextracted with ethyl acetate (3×50 ml.) and the combined ethyl acetate extracts were dried (Na$_2$SO$_4$) and evaporated. The crude material was taken up in saturated sodium bicarbonate (50 ml.) and washed with ethyl acetate. The aqueous phase was acidified with concentrated hydrochloric acid (pH 1) and extracted thoroughly with ethyl acetate. The combined extracts were dried (Na$_2$SO$_4$) and evaporated to give 2.53 g. of crude monoacid as a white foam; R$_f$ (acetic acid/methanol/dichloromethane; 1:1:20)=0.24. A small sample crystallized on standing and was triturated with diisopropyl ether to give crude monoacid as a white crystalline solid; m.p. 85°-89°.

A mixture of the crude monoacid (2.53 g., 7.25 mmole), phenol (3.0 g., 32 mmole) and 48% aqueous hydrobromic acid (30 ml.) was refluxed for 2.25 hours. The cooled mixture was diluted with water (30 ml.) and washed with ethyl acetate (2×30 ml.). The aqueous phase was evaporated to dryness, taken up in water (30 ml.) and evaporated again. This was repeated twice more. Finally, the pale yellow residue was taken up in water and applied to an AG 50 W-X2 (H$^+$ form) column (40 ml. bed volume) and eluted first with water then 5% pyridine-water. The fractions containing the desired product were combined and evaporated to dryness. The solid residue was triturated with acetonitrile to give 0.97 g. of [(2-aminoethyl)hydroxyphosphinyl]acetic acid as a tan crystalline solid; m.p. 225° (dec.); R$_f$ (isopropanol/conc. NH$_4$OH/water; 7:2:1)=0.09.

(d) [[2-(Benzoylamino)ethyl]hydroxyphosphinyl]acetic acid

A suspension of [(2-aminoethyl)hydroxyphosphinyl]acetic acid (0.75 g., 4.49 mmole) in a mixture of dioxane (5 ml.) and water (5 ml.) was cooled in an ice bath and treated with triethylamine (2.0 ml., 14.5 mmole). A clear solution was obtained. The mixture was then treated with benzoyl chloride (0.65 ml., 5.6 mmole) dropwise over a 5 minute period. After stirring at 0° for one hour, the mixture was evaporated to dryness. The residue was taken up in saturated sodium bicarbonate (20 ml.) and washed with ethyl acetate. The aqueous phase was acidified with concentrated hydrochloric acid (pH 1) and extracted with dichloromethane. The dichloromethane extracts were discarded and the aqueous phase evaporated to a small volume. This was then applied to an AG 1-X8 (acetate form) column (30 ml. bed volume) eluting first with water then with 5% acetic acid-water then 1N hydrochloric acid. The product eluted with 1N hydrochloric acid. Fractions containing the product were combined, evaporated to dryness, taken up in water, and lyophilized. The crude product (0.9 g.) was chromatographed on an HP-20 column (1 inch diameter column, 200 ml. bed volume) eluting with a linear gradient of water-acetonitrile (0→100%) at a flow rate of 5 ml./min., collecting 5 ml. fractions. The fractions containing the desired product (Tlc) were combined, evaporated, taken up in water, millipore filtered, and lyophilized to give 0.72 g. of [[(2-benzoylamino)ethyl]hydroxyphosphinyl]acetic acid as a white solid; m.p. 54°-57°; R$_f$ (isopropanol/conc. NH$_4$OH/water; 7:2:1)=0.42.

(e) 1-[[[2-(Benzoylamino)ethyl]hydroxyphosphinyl]acetyl]-L-proline, phenylmethyl ester A suspension of [[(2-(benzoylamino)ethyl]hydroxyphosphinyl]acetic acid (0.6 g., 2.21 mmole) in a mixture of dry tetrahydrofuran (20 ml.) and dry acetonitrile (10 ml.) at room temperature under argon was treated with carbonyldiimidazole (0.4 g., 2.47 mmole). After one hour, the mixture was treated with triethylamine (1.1 ml., 7.95 mmole), and L-proline, phenylmethyl ester, hydrochloride salt (0.65 g., 2.69 mmole), allowed to warm to room temperature and stirred overnight. The reaction mixture was partitioned between ethyl acetate-5% potassium bisulfate (50 ml. each). The aqueous phase was reextracted with ethyl acetate (4×50 ml.). The combined ethyl acetate extracts were washed successively with 5% sodium biphosphate (pH 4.5 buffer) and saturated sodium chloride, dried (Na$_2$SO$_4$) and evaporated. The residue (0.82 g.) was taken up in saturated sodium bicarbonate solution (20 ml.) and washed with ethyl acetate (2×25 ml.). The aqueous phase was acidified with concentrated hydrochloric acid (pH 1), saturated with solid sodium chloride, and extracted with dichloromethane (3×40 ml.). The combined extracts were dried (Na$_2$SO$_4$) to give 0.7 g. of 1-[[[2-(benzoylamino)ethyl]hydroxyphosphinyl]acetyl]-L-proline, phenylmethyl ester as a white foam. R$_f$(acetic acid/methanol/dichloromethane; 1:1:8)=0.28; R$_f$ (isopropanol/conc. NH$_4$OH/water; 7:2:1)=0.76.

(f) 1-[[[2-(Benzoylamino)ethyl]hydroxyphosphinyl]acetyl]-L-proline, dilithium salt A solution of the ester product from part (e) in absolute methanol (60 ml.) is treated with 10% palladium-carbon catalyst (0.3 g.) and hydrogenated in a Parr apparatus at 50 psi for 2.5 hours. The mixture is filtered through Celite and evaporated to dryness. The residue is taken up in 1N lithium hydroxide (3 ml.) and water (4 ml.) and passed down an AG50W-X8 (Li$^+$ form) column (40 ml. bed volume) eluting with water. The fractions containing the desired product are combined and lyophilized. The crude lyophilate is chromatographed on a HP-20 column (1 inch diameter column, 200 ml. bed volume) eluting with a linear gradient of water (100%) to acetonitrile (100%) at a flow rate of 5 ml./min., collecting 5 ml. fractions. Fractions containing the desired product are pooled, evaporated, millipore filtered, and lyophilized to give 1-[[[2-(benzoylamino)ethyl]hydroxyphosphinyl]acetyl]-L-proline, dilithium salt.

EXAMPLES 5-77

Following the procedure of Example 1 but employing the protected amine shown in Col. I and the phosphinic acid ester shown in Col. II, one obtains, after carboxylation, removal of the protecting group and reaction with the acid chloride of Col. III, the carboxylic acid shown in Col. IV. Coupling of the acid of Col IV with the imino or amino acid ester shown in Col. V yields the ester product shown in Col. VI. This ester product can then be converted to a salt or other esters or hydrogenated or hydrolyzed to the corresponding acid compounds, i.e., R$_6$ is hydrogen.

Col. I 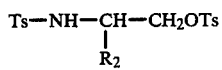
Col. II 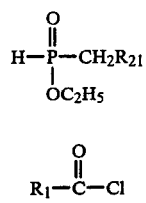
Col. III
$$R_1-\overset{O}{\underset{}{C}}-Cl$$
Col. IV
$$R_1-\overset{O}{\underset{}{C}}-NH-\underset{R_2}{CH}-CH_2-\overset{O}{\underset{OH}{P}}-\underset{}{\overset{R_{21}}{CH}}-COOH$$
Col. V
HX
Col. VI
$$R_1-\overset{O}{\underset{}{C}}-NH-\underset{R_2}{CH}-CH_2-\overset{O}{\underset{OH}{P}}-\underset{}{\overset{R_{21}}{CH}}-\overset{O}{\underset{}{C}}-X$$

| Example | R₁ | R₂ | R₂₁ | X |
|---|---|---|---|---|
| 5 | C₆H₅—CH₂— | C₆H₅—(CH₂)₂— | —H | —N—CH(butyl chain)—COOCH₂C₆H₅ (L), H |
| 6 | 4-CH₃-C₆H₄— | H₃C— | —H | —N—CH(CH₂CH(OH)CH₂)—COOCH₂C₆H₅ (L), H |
| 7 | C₆H₅—(CH₂)₄— | H₅C₂— | —H | —N—CH(CH₂CH(CH₃)CH₂)—COOCH₂C₆H₅ (L), H |
| 8 | 3-Cl-C₆H₄— | H— | —CH₃ | —N—CH(CH₂CH(OCH₃)CH₂)—COOCH₂C₆H₅ (L), H |
| 9 | C₆H₅—(CH₂)₆— | H₃C— | —H | —N—CH(CH₂CH(SC₂H₅)CH₂)—COOC(CH₃)₃ (L), H |
| 10 | H₃C— | C₆H₅— | —C₂H₅ | —N—CH(CH₂CH(Cl)CH₂)—COOCH₂C₆H₅ (L), H |

-continued
| Example | R₁ | R₂ | R₂₁ | X |
|---|---|---|---|---|
| 11 | H₅C₂— | CH₂–Ph | —CH₃ | 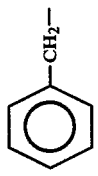 |
| 12 | (H₃C)₃C— | —H | —H |  |
| 13 | F₃C— | CH₂–Ph | —(CH₂)₂–Ph | 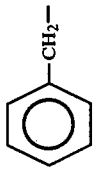 |
| 14 | Cl₃CH₂C— | —CH₃ | —H |  |
| 15 | cyclohexyl | CH₂–Ph | —CH(Ph)₂ | 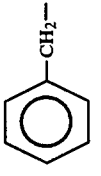 |
| 16 | cyclopentyl–CH₂— | Ph | —H | 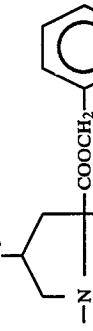 |

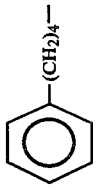

-continued
| Example | R₁ | R₂ | R₂₁ | X |
|---|---|---|---|---|
| 22 | 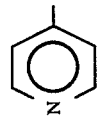 | H₃C— | —H | 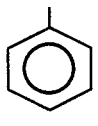 |
| 23 | 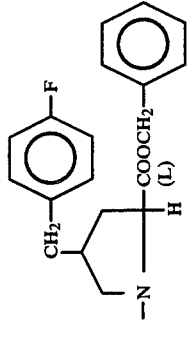 | H— | —CH₃ | 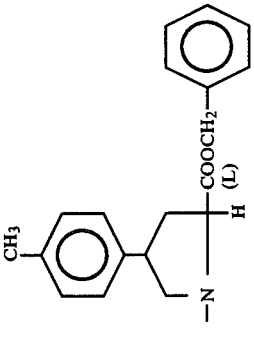 |
| 24 | 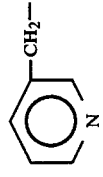 | 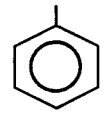 | —H | 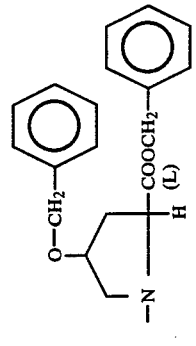 |
| 25 | 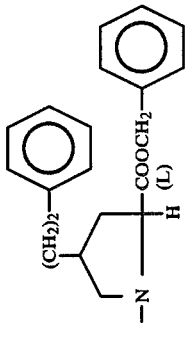 |  | —H |  |

-continued
| Example | R₁ | R₂ | R₂₁ | X |
|---|---|---|---|---|
| 26 | 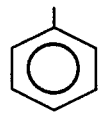 |  | —H |  |
| 27 | 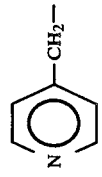 | 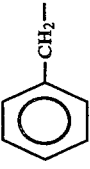 | —H |  |
| 28 | 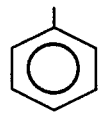 | 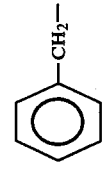 | —H |  |
| 29 | 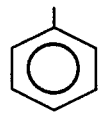 |  | —H |  |
| 30 | 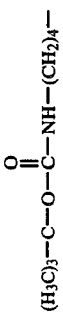 | 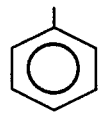 | —H | 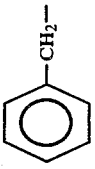 |

-continued

| Example | R₁ | R₂ | R₂₁ | X |
|---|---|---|---|---|
| 31 | 2-thienyl | -(CH₂)₃-C₆H₅ | -H | -N[CH₂CH(O-C₆H₄-C₆H₅)CH₂-]CH(COOCH₂C₆H₅)(L)H |
| 32 | 2-furyl | H₃C- | -H | -N[CH(2-naphthylthio)CH₂-]CH(COOC(CH₃)₃)(L)H |
| 33 | H₂C=CH- | -CH₂-C₆H₅ | -H | -N[CH(5-methyl-2-thienyl)CH₂-]CH(COOC(CH₃)₃)(L)H |
| 34 | C₆H₅ | -CH₂-C₆H₅ | -CH₃ | -N[CH(5-methyl-2-furyl)CH₂-]CH(COOCH₂C₆H₅)(L)H |
| 35 | C₆H₅ | -CH₂-C₆H₅ | -H | piperidine-2-COOCH₂C₆H₅ (L) |

-continued
| Example | R₁ | R₂ | R₂₁ | X |
|---------|----|----|-----|---|
| 36 | phenyl | benzyl | —H | 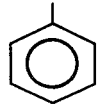 |
| 37 | phenyl | benzyl | —H | 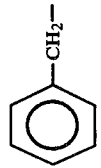 |
| 38 | phenyl | benzyl | —H | 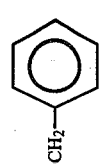 |
| 39 | phenyl | benzyl | —H |  |
| 40 | phenyl | benzyl | —H | 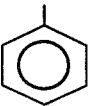 |

| Example | R₁ | R₂ | R₂₁ | X |
|---|---|---|---|---|
| 41 | PhCH₂– | Ph– | –H | –N(CH₂CH₂CH(SPh)–)CH(COOC(CH₃)₃)H (L) |
| 42 | Ph– | Ph– | –H | –N(CH₂CH₂CH(OCH₂Ph)–)CH(COOCH₂Ph)H (L) |
| 43 | PhCH₂– | PhCH₂– | –H | –N(CH₂CH₂CH(SCH₃)–)CH(COOC(CH₃)₃)H (L) |
| 44 | Ph– | PhCH₂– | –H | –N(–C(=O)CH₂CH₂–)CH(COOCH₂Ph)H (L) |
| 45 | Ph– | PhCH₂– | –H | –N(CH₂CH₂CH(Ph)–)CH(COOCH₂Ph)H (L) |
| 46 | Ph– | PhCH₂– | –H | –N(CH₂CF₂–)CH(COOCH₂Ph)H (L) |

-continued
| Example | R₁ | R₂ | R₂₁ | X |
|---|---|---|---|---|
| 47 | phenyl | benzyl (CH₂-Ph) | —H | 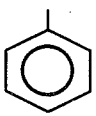 |
| 48 | phenyl | benzyl (CH₂-Ph) | —H | 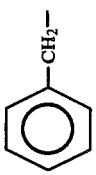 |
| 49 | phenyl | benzyl (CH₂-Ph) | —H | 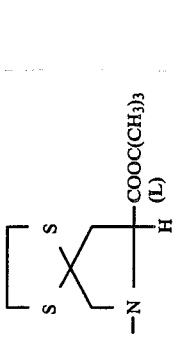 |
| 50 | phenyl | benzyl (CH₂-Ph) | —H | 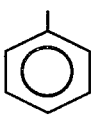 |
| 51 | phenyl | benzyl (CH₂-Ph) | —H | 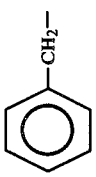 |

-continued

| Example | R₁ | R₂ | R₂₁ | X |
|---|---|---|---|---|
| 52 | phenyl | benzyl (CH₂-Ph) | —H | -S-CH₂-C(-N)(H)-COOC(CH₃)₃ (L) |
| 53 | phenyl | benzyl (CH₂-Ph) | —H | -S-C(CH₃)₂-C(-N)(H)-COOC(CH₃)₃ (L) |
| 54 | phenyl | benzyl (CH₂-Ph) | —H | 2-hydroxybenzyl-S-CH₂-C(-N)(H)-COOC(CH₃)₃ (L) |
| 55 | phenyl | benzyl (CH₂-Ph) | —H | benzyl-S-CH₂-C(-N)(H)-COOC(CH₃)₃ (L) |
| 56 | phenyl | benzyl (CH₂-Ph) | —H | -NH-CH₂-COOCH₂-Ph |
| 57 | phenyl-(CH₂)₄- | benzyl (CH₂-Ph) | —H | -NH-CH(CH₂CH(CH₃)₂)-COOCH₂-Ph (L) |

-continued

| Example | R₁ | R₂ | R₂₁ | X |
|---|---|---|---|---|
| 58 | phenyl | H₅C₂— | —H | —N(CH₃)—CH₂—COOCH₂—phenyl |
| 59 | thienyl | benzyl (—CH₂—phenyl) | —H | —N(cyclopentyl)—CH₂—COOCH₂—phenyl |
| 60 | furyl | benzyl (—CH₂—phenyl) | —H | —N(—(CH₂)₂—phenyl)—CH₂—COOCH₂—phenyl |
| 61 | H₃C—(CH₂)₅— | benzyl (—CH₂—phenyl) | —H | —NH—CH(CH₃)—COOCH₂—phenyl (L) |
| 62 | phenyl—(CH₂)₆— | H₅C₂— | —H | —NH—CH(CH₂—phenyl)—COOCH₂—phenyl (L) |

-continued
| Example | R₁ | R₂ | R₂₁ | X |
|---|---|---|---|---|
| 63 |  | 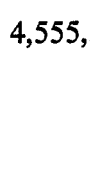 | —H |  |
| 64 |  | 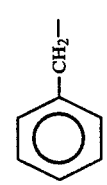 | —H | 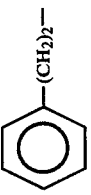 |
| 65 | 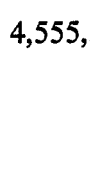 | 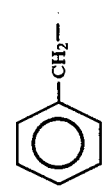 | —CH₃ | 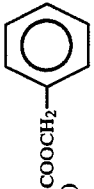 |

-continued

| Example | $R_1$ | $R_2$ | $R_{21}$ | X |
|---|---|---|---|---|
| 66 | phenyl | benzyl | —H | —NH—CH(L)—COOCH$_2$-phenyl, with CH$_2$ side chain bearing pyrrole (N=CH—N—CH$_2$-phenyl) |
| 67 | cyclohexyl | benzyl | —H | —NH—CH(L)—COOCH$_2$-phenyl, (CH$_2$)$_4$—NHCOCH(=O)—phenyl side chain |
| 68 | 2-thienyl-CH$_2$— | benzyl | —H | —NH—CH(L)—COOCH$_2$-phenyl, CH$_2$—S—CH$_2$-phenyl side chain |
| 69 | 2-furyl-CH$_2$— | benzyl | —H | —NH—CH(L)—COOCH$_2$-phenyl, (CH$_2$)$_2$—S—CH$_3$ side chain |
| 70 | phenyl | 2-thienyl-CH$_2$— | —H | —NH—CH(L)—COOCH$_2$-phenyl, (CH$_2$)$_3$NHC(NH)=NHC—NHNO$_2$ side chain |

-continued
| Example | R₁ | R₂ | R₂₁ | X |
|---------|-----|-----|-----|---|
| 71 | H₅C₂— | 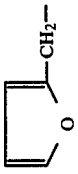 | —H |  |
| 72 |  | 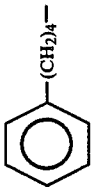 | —H | 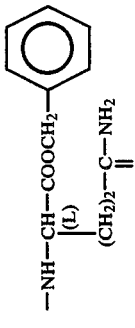 |
| 73 |  | 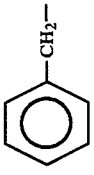 | —H | 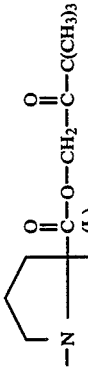 |
| 74 |  | 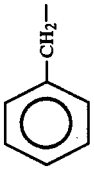 | —H | 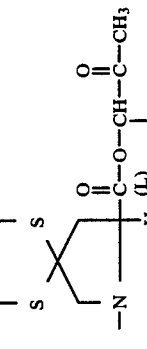 |
| 75 |  | 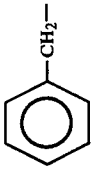 | —H | 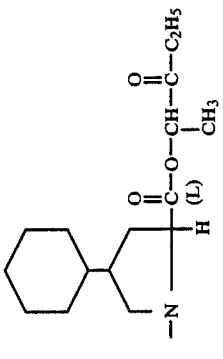 |

-continued
| Example | R₁ | R₂ | R₂₁ | X |
|---|---|---|---|---|
| 76 | C₆H₅– | C₆H₅–CH₂– | –H | 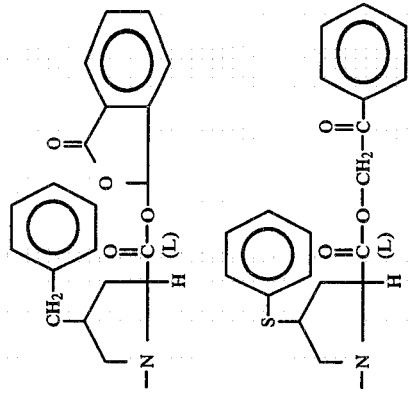 |
| 77 | C₆H₅– | C₆H₅–CH₂– | –H | 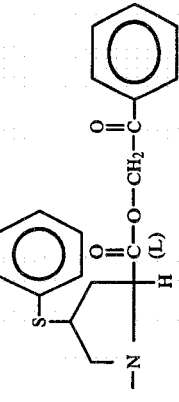 |

Reduction of the product of Example 15 yields the corresponding 4-amino product. Similarly, the 4-keto product of Example 13 can be reductively aminated to yield various 4-substituted amino products. The $R_1$ and $R_2$ protecting groups shown in Examples 28 and 29 and the $R_5$ protecting groups shown in Examples 63, 64, 66–68, and 70 are removed following completion of the coupling reaction.

EXAMPLE 78

(±)-1-[[[2-(Benzoylamino)-3-phenylpropyl]hydroxyphosphinyl]acetyl]-L-proline, dilithium salt (a) α-Benzylacrylic acid, ethyl ester Diethyl benzylmalonate (25 g., 0.10 mole) in ethanol (65 ml.) at 0° in an argon atmosphere was treated dropwise with potassium hydroxide (5.6 g., 1.0 eq.) in ethanol (65 ml.) over a 15 minute period. After stirring for 72 hours at 25° the ethanol was stripped and the residue was acidified with concentrated hydrochloric acid (10 ml.). The resulting white oil was extracted into ethyl acetate then washed with brine, dried (MgSO$_4$), and evaporated to give 24 g. of clear liquid ethyl benzylmalonic acid. Tlc (hexane:ethyl acetate; 3:1) major spot at $R_f=0.1$.

The ethyl benzylmalonic acid (24 g., 0.10 mole), paraformaldehyde (2.5 g., 0.1 mole), pyridine (18 ml.), and piperidine (1.0 ml., 0.1 eq.) were refluxed for 1.5 hours; gas evolution was observed. The reaction mixture was diluted with ether and then washed with water, 1N hydrochloric acid, water, brine, dried (MgSO$_4$), and evaporated to give a residue (23 g.). Distillation of the residue gives 13.5 g. of α-benzylacrylic acid, ethyl ester as a clear liquid at head temperature 70°–75° (0.1 mm Hg.). Tlc (hexane:ethyl acetate; 4:1) one spot at $R_f=0.7$.

(b) α-Benzylacrylic acid

A mixture of α-benzylacrylic acid, ethyl ester (13.5 g., 0.071 mole), ethanol (140 ml.), and 1N sodium hydroxide (140 ml., 2 eq.) was stirred under argon at room temperature for 12 hours. The ethanol and some water was stripped and the residue washed with ethyl acetate and then acidified with concentrated hydrochloric acid to pH 1.0. The resulting oil was extracted into ethyl acetate, then washed with brine, dired (MgSO$_4$), and evaporated to give 9.9 g. of α-benzylacrylic acid as a white crystalline solid; m.p. 61°–62°. Tlc (ethyl acetate:-hexane; 3:1) major spot at $R_f=0.8$.

(c) [(2-Carboxy-3-phenylpropyl)ethoxyphosphinyl]acetic acid, methyl ester

A mixture of α-benzylacrylic acid (5.0 g., 30.8 mmole) and carbomethoxymethyldichlorophosphine (4.5 ml., 1.6 eq.) under argon was heated at 65° for 18 hours. The flask was then equipped with a short path still, acetic anhydride (6.4 ml., 2.0 eq.) was added, and the temperature was increased to 85°. After 2.5 hours, acetyl chloride was no longer distilling and the excess acetic anhydride and acetyl chloride were removed in vacuo. Ethanol (6 ml.) was added to the residue and the resulting mixture was stirred at 60° for 2 hours. The ethanol was then stripped to leave a residue (12.4 g.) which was chromatographed on silica (300 g.) eluting with (dichloromethane/acetic acid/methanol; 100/2.5/2.5) to give 2.2 g. of [(2-carboxy-3-phenylpropyl)ethoxyphosphinyl]acetic acid, methyl ester as a colorless oil. Tlc (dichloromethane/acetic acid/methanol; 100/5/5) single spot at $R_f=0.5$.

(d) [Ethoxy[3-phenyl-2-[[(phenylmethoxy)carbonyl]amino]propyl]phosphinyl]acetic acid, methyl ester The methyl ester product from part (c) (2.1 g., 6.4 mmole) in dry toluene (10 ml.) was treated with carbonyldiimidazole (1.0 g., 1.0 eq.) at 0° under argon. After stirring for one hour, azidotrimethylsilane (1.3 ml., 1.5 eq.) was added. After 40 minutes at room temperature, the reaction mixture was diluted with cold toluene and then washed with 5% potassium bisulfate (twice), brine, dried (MgSO$_4$), and evaporated. The residue was taken up in dry toluene (10 ml.) and heated at 100° for 1 hour; gas evolution began at ~80°. Benzyl alcohol (1.4 ml., 2.0 eq.) was added and the reaction mixture was heated for an additional 2 hours. The toluene was stripped to give a residue (1.4 g.) which was chromatographed on silica (130 g.) eluting with ethyl acetate to give 0.89 g. of [ethoxy[3-phenyl-2-[[(phenylmethoxy)carbonyl]amino]propyl]phosphinyl]acetic acid, methyl ester as an oil. Tlc (ethyl acetate) single spot at $R_f=0.3$.

(e) [Ethoxy[3-phenyl-2-[[(phenylmethoxy)carbonyl]amino]propyl]phosphinyl]acetic acid A mixture of the diester product of part (d) (0.89 g., 2.0 mmole), 1N sodium hydroxide (2.0 ml., 1 eq.) and dioxane (2.5 ml.) was stirred at room temperature in an argon atmosphere for 2 hours. The reaction mixture was diluted with water and then washed with ether. The aqueous phase was acidified with concentrated hydrochloric acid and the resulting oil was extracted into ethyl acetate (twice), washed with brine, dried (MgSO$_4$), and evaporated to give 0.81 g. of [ethoxy[3-phenyl-2-[[(phenylmethoxy)carbonyl]amino]propyl]phosphinyl]acetic acid as a foam. Tlc (dichloromethane/acetic acid/methanol; 100/5/5) major spot at $R_f=0.5$.

(f) 1-[[Ethoxy[3-phenyl-2-[[(phenylmethoxy)carbonyl]amino]propyl]phosphinyl]acetyl]-L-proline, 1,1-dimethylethyl ester The mono ester product from part (e) (0.81 g., 1.94 mmole) in tetrahydrofuran (4 ml.) at 0° in an argon atmosphere was treated with carbonyldiimidazole (0.31 g., 1.0 eq.). After one hour, triethylamine (0.3 ml., 1.1 eq.) then L-proline, t-butyl ester (0.43 g., 1.3 eq.) were added to the above mixture. After stirring at room temperature for 16 hours, the reaction mixture was diluted with ethyl acetate and then washed with water, 5% sodium bicarbonate, 5% potassium bisulfate (twice), brine, dried (MgSO$_4$), and evaporated to give 0.9 g of 1-[[ethoxy[3-phenyl-2-[[(phenylmethoxy)carbonyl]amino]propyl]phosphinyl]acetyl]-L-proline, 1,1-dimethylethyl ester as a foam. Tlc (dichloromethane/acetic acid/methanol; 100/5/5) major spot at $R_f=0.5$.

(g) 1-[[(2-Amino-3-phenylpropyl)ethoxyphosphinyl]acetyl]-L-proline, 1,1-dimethylethyl ester The product from part (f) (0.9 g., 1.57 mmole) in methanol (50 ml.) was treated with 10% palladium on carbon catalyst (100 mg.) and hydrogenated in a Parr apparatus at 36 psi for 16 hours. The catalyst was filtered off (Celite bed) and the solvent stripped to give 0.7 g. of 1-[[(2-amino-3-phenylpropyl)ethoxyphosphinyl]acetyl]-L-proline, 1,1-dimethylethyl ester as an oil. Tlc (dichloromethane/methanol/acetic acid; 8/1/1) one spot at $R_f=0.3$.

(h) 1-[[[2-(Benzoylamino)-3-phenylpropyl]ethoxyphosphinyl]acetyl]-L-proline, 1,1-dimethylethyl ester A mixture of the product from part (g) (700 mg., 1.57 mmole), tetrahydrofuran (95 ml.) and pyridine (0.4 ml., 3.0 eq.) at 0° under argon was treated with benzoyl chloride (0.3 ml., 1.7 eq.). After stirring at room temperature for 2 hours the reaction mixture was diluted with ethyl acetate, then washed with water, 5% potassium bisulfate, 5% sodium bicarbonate, brine, dried (MgSO$_4$) and evaporated. The residue (900 mg.) was chromatographed on silica (60 g.) eluting with (dichloromethane/acetone; 1/1). The solvent was stripped to give 730 mg. of 1-[[[2-(benzoylamino)-3-phenylpropyl]ethoxyphosphinyl]acetyl]-L-proline, 1,1-dimethylethyl ester as a foam. Tlc (dichloromethane/acetone; 1/1) isomers at $R_f$ 0.3 and 0.4.

(i) 1-[[[2-(Benzoylamino)-3-phenylpropyl]hydroxyphosphinyl]acetyl]-L-proline, 1,1-dimethylethyl ester The diester product from part (h) (730 mg., 1.34 mmole) in dry dichloromethane (2 ml.) was treated with bromotrimethylsilane (0.3 ml., 1.5 mmole) in an argon atmosphere. After 16 hours the excess dichloromethane and excess bromotrimethylsilane was removed in vacuo. The residue was diluted with water and ethyl acetate and stirred for 5 minutes. The ethyl acetate phase was washed with brine, dried (MgSO$_4$), and evaporated to give 630 mg. of 1-[[[2-(benzoylamino)-3-phenylpropyl]hydroxyphosphinyl]acetyl]-L-proline, 1,1-dimethylethyl ester. Tlc (dichloromethane/methanol/acetic acid) major spot at $R_f=0.4$.

(j) 1-[[[2-(Benzoylamino)-3-phenylpropyl]hydroxyphosphinyl]acetyl]-L-proline

A mixture of the mono ester product from part (i) (630 mg., 1.22 mmole), anisole (0.2 ml., 1.5 eq.), and trifluoroacetic acid (5 ml.) was stirred under argon at room temperature for 2.5 hours. The trifluoroacetic acid and anisole were removed in vacuo and the residue was then dissolved in saturated sodium bicarbonate and washed with ether (twice). The aqueous phase was acidified with concentrated hydrochloric acid and the resulting oil was extracted into ethyl acetate. The ethyl acetate phase was washed with water (twice), brine, dried (MgSO$_4$), and evaporated to give 500 mg. of 1-[[[2-(benzoylamino)-3-phenylpropyl]hydroxyphosphinyl]acetyl]-L-proline as a foam. Tlc (butanol/water/acetic acid; 4/1/1) major spot at $R_f=0.4$.

(k) 1-[[[2-(Benzoylamino)-3-phenylpropyl]hydroxyphosphinyl]acetyl]-L-proline, dilithium salt The diacid product from part (j) (500 mg., 1.1 mmole) was dissolved in 1N lithium hydroxide (1.5 ml., 1.5 eq.) and water (40 ml.). The resulting solution was run through an AG50W-X8 (Li$^+$) resin column eluting with water. The fractions containing the desired product were combined, filtered (millipore) and lyophilized. The resulting dense white solid (500 g.) was purified on a Sephadex LH-20 (65 g., one inch column) eluting with water at a flow rate of 1 ml./min. The desired fractions were combined, filtered (millipore) and lyophilized to give 220 mg. of 1-[[[2-(benzoylamino)-3-phenylpropyl]hydroxyphosphinyl]acetyl]-L-proline, dilithium salt as a fluffy white solid; $[\alpha]_D^{25}=-35.°$ (c=1.12, methanol); Tlc (butanol/water/acetic acid; 4/1/1) one spot at $R_f=0.4$; electrophoresis pH 6.5, 2000 V, 35 minutes, single spot at +4.2 cm., visualized with carboxyl reagent.

Anal. calc'd. for $C_{23}H_{25}N_2O_6PLi_2 \cdot 2H_2O$: C, 54.56; H, 5.77; N, 5.53; P, 6.1. Found: C, 54.52; H, 5.23; N, 5.44; P, 5.9.

EXAMPLES 79-94

Following the procedure of Example 78 but employing the acrylic acid shown in Col. I, the dichlorophosphine shown in Col. II, and the alcohol shown in Col. III one obtains the phosphinic intermediate shown in Col. IV. The intermediate of Col. IV is then converted to the acid azide, subjected to Curtius rearrangement, and reacted with benzyl alcohol or t-butanol to yield the diester intermediate of formula V. Hydrogenation of the intermediate of formula V with palladium on carbon catalyst or treatment with acid (t-butanol case) followed by reaction with the acid chloride of formula VI yields the diester of formula VII. Removal of the carboxylic acid ester and coupling with the imino or amino acid ester of Col. VIII yields the diester product of Col. IX. This diester product can then be treated to remove the ester group and yield the corresponding diacid (R$_3$ and R$_6$ are hydrogen) and then converting to a salt or other esters.

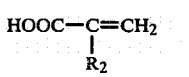

Col. I

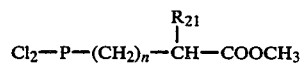

Col. II

Col. III

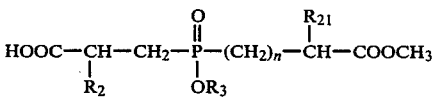

Col. IV

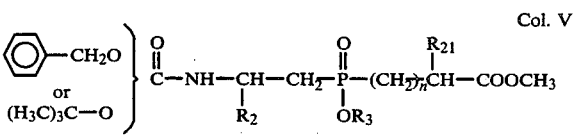

Col. V

Col. VI

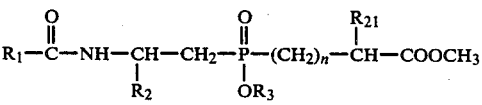

Col. VII

HX

Col. VIII

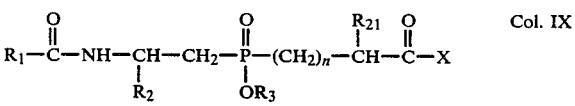

Col. IX

| Example | R₁ | R₂ | R₃ | n | R₂₁ | X |
|---|---|---|---|---|---|---|
| 79 | C₆H₅— | C₆H₅—CH₂— | —C₂H₅ | 1 | —H | —N(H)—CH(L)—COOC(CH₃)₃ with (CH₂)₃ chain |
| 80 | C₆H₅—(CH₂)₄— | H₃C— | —CH₂—C₆H₅ | 1 | —H | —N(H)—CH(L)—COOC(CH₃)₃ with CH₂CH[O-naphthyl] side chain |
| 81 | 2-thienyl— | C₆H₅—CH₂— | —C₂H₅ | 1 | —CH₃ | —N(H)—CH(L)—COOC(CH₃)₃ with spiro dithiolane |
| 82 | 2-furyl—CH₂— | C₆H₅—(CH₂)₄— | —C₂H₅ | 1 | —CF₃ | —N(H)—CH(L)—COOC(CH₃)₃ with CH₂-cyclohexyl |
| 83 | H₃CO—C₆H₄— | H₅C₂— | —C₂H₅ | 1 | —H | —N(H)—CH(L)—COOC(CH₃)₃ with CH₂CH(S-C₆H₅) |
| 84 | C₆H₅— | (H₃C)₃C—O—C(O)—NH—(CH₂)₄— | —C₂H₅ | 1 | —H | —N(H)—CH(L)—COOC(CH₃)₃ with CH₂CH(CH₂—C₆H₅) |
| 85 | C₆H₅—CH₂—O—C(O)—NH—(CH₂)₂— | C₆H₅—CH₂— | —C₂H₅ | 1 | —H | piperidine-N—CH(L)(H)—COOC(CH₃)₃ |
| 86 | H₃C— | 2-thienyl—CH₂— | —C₂H₅ | 1 | —H | tetrahydroisoquinoline-N—CH(L)(H)—COOC(CH₃)₃ |
| 87 | H₃C—(CH₂)₆— | 4-H₃C—C₆H₄—CH₂— | —C₂H₅ | 0 | —H | —NH—CH₂—COOC(CH₃)₃ |
| 88 | cyclohexyl— | 2-furyl—CH₂— | —C₂H₅ | 1 | —H | —NH—CH(CH₂—C₆H₅)—COOC(CH₃)₃ |

-continued

| Example | R₁ | R₂ | R₃ | n | R₂₁ | X |
|---|---|---|---|---|---|---|
| 89 | ⌬—(CH₂)₆— | ⌬—(CH₂)₂— | —C₂H₅ | 1 | —H | —N(CH₃)—CH₂—COOC(CH₃)₃ |
| 90 | ⌬— | ⌬—CH₂— | —C₂H₅ | 1 | —H | —NH—CH(CH₂-Ar)—COOCH₂—⌬ (L), where Ar = 3,4-bis(benzyloxy)phenyl |
| 91 | ⌬— | ⌬—CH₂— | —C₂H₅ | 1 | —H | —NH—CH(CH₂-Ar')—COOCH₂—⌬ (L), where Ar' = 4-(benzyloxy)phenyl |
| 92 | H₅C— | ⌬— | —C₂H₅ | 1 | CH₃ | —NH—CH(CH₂-indolyl)—COOC(CH₃)₃ (L) |
| 93 | ⌬— | —H | —C₂H₅ | 1 | —H | —NHCH(COOC(CH₃)₃)—(CH₂)₃—NHC(=NH)NHNO₂ |
| 94 | ⌬— | ⌬—CH₂ | —C₂H₅ | 1 | —H | —N(pyrrolidine ring)—C(=O)—O—CH₂—C(=O)—C₂H₅ (L) |

The R₁ and R₂ protecting groups shown in Examples 84 and 85 and the R₅ protecting groups shown in Examples 90 and 91, and 93 are removed following completion of the coupling reaction.

EXAMPLE 95

[[2-(Benzoylamino)-3-phenylpropyl]hydroxyphosphinyl]-L-alanyl-L-proline, dilithium salt (a) 4-Methylbenzenesulfonic acid, 2-[[(4-methylphenyl)sulfonyl]amino]-3-phenylpropyl ester A solution of d,l-phenylalaninol, hydrochloride (9.4 g., 50.1 mmole) in dry pyridine (35 ml.) at 0° (ice bath) was treated with p-toluenesulfonyl chloride (19.4 g., 102 mmole) in small portions over a 15 minute period. The mixture was allowed to come to room temperature and stirred overnight. The mixture was evaporated to dryness and the residue partitioned between ethyl acetate and 5% potassium bisulfate. The ethyl acetate layer was washed successively with 5% potassium bisulfate, saturated sodium bicarbonate and saturated sodium chloride, dried (Na₂SO₄), and evaporated. The dark residue was filtered through a pad of silica gel eluting with dichloromethane then dichloromethane-ethyl acetate (1:1). Evaporation of the solvents and trituration of the residue with ether gave 13.93 g. of 4-methylbenzenesulfonic acid, 2-[[(4-methylphenyl)sulfonyl]amino]-3-phenylpropyl ester as white crystals; m.p. 95°–96°; R_f (ethyl acetate/hexane; 1:2)=0.39. A sample recrystallized from diisopropyl ether had m.p. 96°–98°.

(b) [2-[[(4-Methylphenyl)sulfonyl]amino]-3-phenylpropyl]-phosphonic acid, diethyl ester A solution of diethylphosphite (7.3 g., 52.9 mmole) in dry tetrahydrofuran (100 ml.) was treated with sodium hydride 50% oil dispersion (2.20 g., 45.8 mmole) in small portions under argon. The mixture was then refluxed for 30 minutes, cooled to room temperature, and treated with 4-methylbenzenesulfonic acid, 2-[[(4-methylphenyl)sulfonyl]amino]-3-phenylpropyl ester (6.9 g., 15 mmole). After 15 minutes, a white solid had separated; additional tetrahydrofuran (75 ml.) was added and stirring continued overnight. After stirring at room temperature overnight, the mixture was refluxed for one hour, cooled and partitioned between ethyl acetate (75 ml.) and 5% potassium bisulfate (50 ml.).

The ethyl acetate phase was washed successively with 5% potassium bisulfate, saturated sodium bicarbonate and saturated sodium chloride, dried (Na₂SO₄), and evaporated. The residue was triturated with hexane to give 5.9 g. of [2-[[(4-methylphenyl)sulfonyl]amino]-3-phenylpropyl]phosphonic acid, diethyl ester as an off white solid; m.p. 86°–89°; R$_f$ (ethyl acetate)=0.48. A sample recrystallized from diisopropyl ether had m.p. 94°–95°.

(c) (2-Amino-3-phenylpropyl)phosphonic acid

A mixture of [2-[[(4-methylphenyl)sulfonyl]amino]-3-phenylpropyl]phosphonic acid, diethyl ester (5.9 g., 13.9 mmole), phenol (8.0 g., 85.1 mmole), and 48% aqueous hydrobromic acid (50 ml.) was refluxed for 5.5 hours. The cooled mixture was diluted with water (50 ml.) and washed with ethyl acetate (2×50 ml.). The aqueous phase was evaporated to dryness, taken up in water (30 ml.) and evaporated again. This was repeated twice more. Finally, the residue was taken up in water and applied to an AG50W-X2 (H+ form) column (60 ml. bed volume) and eluted first with water then with 5% pyridine-water. The fractions containing the desired product were combined and evaporated to dryness. The solid residue was triturated with acetonitrile to give 2.55 g of (2-amino-3-phenylpropyl)phosphonic acid as an off-white crystalline solid; m.p. 347° (dec.); R$_f$(isopropanol/conc. NH₄OH/water; 7:2:1)=0.27.

(d) (2-Phthalimido-3-phenylpropyl)phosphonic acid

A mixture of (2-amino-3-phenylpropyl)phosphonic acid (2.0 g., 9.3 mmole) and phthalic anhydride (1.55 g., 10.5 mmole) was fused in a flask under argon at 195°–200° (bath temperature for 1.5 hours. The glassy dark residue was refluxed with ethyl acetate (25 ml.) until the glassy residue had dissolved and a fluffy crystalline solid had separated. The cooled mixture was diluted with diethyl ether (25 ml.) and filtered. The solid was washed thoroughly with diethyl ether and dried to give 2.87 g. of (2-phthalimido-3-phenylpropyl)-phosphonic acid as an off-white crystalline solid; m.p. 127°–130°. A sample crystallized from ethyl acetate m.p. 129°–131°; R$_f$(isopropanol/conc. NH₄OH/water; 7:2:1)=0.33.

(e)
[(2-Phthalimido-3-phenylpropyl)(phenylmethoxy)phosphinyl]-L-alanyl-L-proline, phenylmethyl ester A suspension of (2-phthalimido-3-phenylpropyl)-phosphonic acid (2.6 g., 7.54 mmole) in dry benzene (10 ml.) was treated with phosphorus pentachloride (3.3 g., 1.59 mmole) and stirred at room temperature under argon for 45 minutes. The mixture was then refluxed for 15 minutes, cooled and evaporated to dryness at room temperature (0.5 mm. of Hg.). The residue was taken up in dry tetrahydrofuran (10 ml.) and treated dropwise with a solution of benzyl alcohol (0.81 g., 7.5 mmole) and triethylamine (1.05 ml., 7.59 mmole) in dry tetrahydrofuran (5 ml.) over a period of 20 minutes. The mixture was stirred at room temperature for 30 minutes and then treated with L-alanine-L-proline, phenylmethyl ester, hydrochloride salt (2.4 g., 7.68 mmole). The resulting suspension was cooled in an ice bath and treated dropwise with a solution of triethylamine (4.5 ml., 32.5 mmole) in tetrahydrofuran (8 ml.) over a period of 15 minutes. The mixture was warmed to room temperature, stirred for one hour, diluted with ethyl acetate, filtered, and evaporated. The residue was taken up in ethyl acetate (50 ml.) and washed successively with 5% potassium bisulfate, saturated sodium bicarbonate and saturated sodium chloride, dried (Na₂SO₄), and evaporated. The residue (5 g.) was purified by flash chromatography on silica gel (90 g.) eluting with acetone-hexane (1:2) to give 2.5 g. of [(2-phthalimido-3-phenylpropyl)(phenylmethoxy)phosphinyl]-L-alanyl-L-proline, phenylmethyl ester as a white foam; R$_f$(acetone/hexane; 1:1)=0.38.

(f)
[[2-(Benzoylamino)-3-phenylpropyl](phenylmethoxy)-phosphinyl]-L-alanyl-L-proline, phenylmethyl ester A solution of the product from part (e) (1.44 g., 2.08 mmole) in dioxane (10 ml.) was treated with hydrazine hydrate (200 μL., 4.12 mmole) and stirred at room temperature under argon. After 22 hours at room temperature, additional hydrazine hydrate (50 μl.) was added and stirring continued for 4 hours. The mixture was then partitioned between ethyl acetate-water and the ethyl acetate phase was washed with water and saturated sodium chloride, dried (Na₂SO₄), and evaporated. The residue (1.5 g.) was taken up in dry toluene and refluxed for one hour. The mixture was filtered, treated with triethylamine (0.75 ml., 5.42 mmole) and benzoyl chloride (0.25 ml., 2.15 mmole) and stirred at room temperature for 30 minutes. The mixture was diluted with ethyl acetate, washed successively with 5% potassium bisulfate, saturated sodium bicarbonate, and saturated sodium chloride, dried (Na₂SO₄), and evaporated. The residue was chromatographed on silica gel (90 g.) eluting first with ethyl acetate then acetone-ethyl acetate (1:5) to give 0.95 g. of [[2-(benzoylamino)-3-phenylpropyl](phenylmethoxy)phosphinyl]-L-alanyl-L-proline, phenylmethyl ester as a white foam. Tlc (ethyl acetate) showed two spots (isomers, ~1:1) R$_f$=0.22, 0.31.

(g)
[[2-(Benzoylamino)-3-phenylpropyl]hydroxyphosphinyl]-L-alanyl-L-proline, dilithium salt A solution of the diester product from part (f) in methanol is treated with water, triethylamine, and 10% palladium on carbon catalyst and hydrogenated in a Parr apparatus at 50 psi for about 2 hours. The mixture is filtered through Celite and the filter cake is washed thoroughly with methanol. The combined filtrates are evaporated to dryness and the residue is taken up in water and applied to an AG-50W-X8 (Li+) column (50 ml. settled bed volume) eluting with water. Fractions containing the desired product are combined and lyophilized to give [[2-(benzoylamino-3-phenylpropyl]hydroxyphosphinyl]-L-alanyl-L-proline, dilithium salt.

EXAMPLES 96–122

Following the procedure of Example 95 but employing the protected amine shown in Col. I and the phosphinic diester shown in Col. II, one obtains, after removal of the tosyl protecting group and reaction with phthalic anhydride, the phosphonic acid shown in Col. III. The acid of Col. III is then converted to the phosphinic acid ester chloride shown in Col. IV which is then coupled with the peptide or imino or amino acid or ester shown in Col. V to yield the intermediate shown in Col. VI. Removal of the phthalidyl group and reaction with the acid chloride shown in Col. VII yields the product shown in Col. VIII.

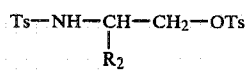 Col. I
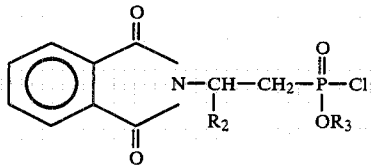 Col. IV
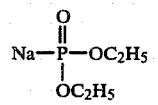 Col. II
 Col. V
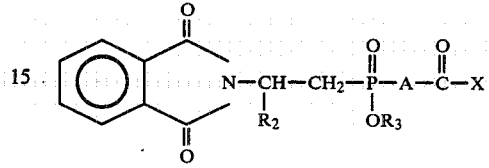 Col. VI
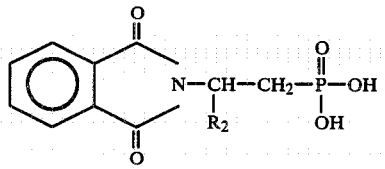 Col. III
$R_1-\overset{O}{\overset{\|}{C}}-Cl$ Col. VII
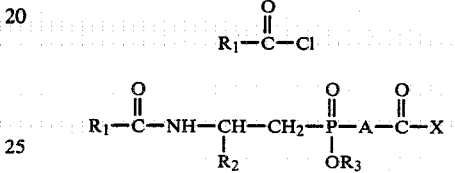 Col. VIII

| Example | R₁ | R₂ | R₃ | A | X |
|---|---|---|---|---|---|
| 96 | PhCH₂— | Ph(CH₂)₂— | H₅C₂— | —NH—CH(CH₃)— (L) | PhS-CH(CH₂-)-CH(H)(COOCH₂Ph)-N- (L) |
| 97 | 4-CH₃-C₆H₄— | Ph(CH₂)₃— | PhCH₂— | —NH—CH(CH₃)— (L) | C₆H₁₁-CH(CH₂-)-CH(H)(COOCH₂Ph)-N- (L) |
| 98 | Ph(CH₂)₄— | Ph— | H₅C₂— | —NH—CH(CF₃)— (L) | (S,S-spiro)C(CH₂-)-CH(H)(COOCH₂Ph)-N- (L) |
| 99 | 4-CH₃-C₆H₄— | H₅C₂— | PhCH₂— | —NH—CH₂— | (O,O-spiro)C(CH₂-)-CH(H)(COOCH₂Ph)-N- (L) |

-continued

| Example | R₁ | R₂ | R₃ | A | X |
|---|---|---|---|---|---|
| 100 | (H₃C)₃C— | 4-Cl-C₆H₄-CH₂— | C₆H₅-CH₂— | —NH—CH(CH₂-C₆H₅)— (L) | —N[CH₂-CH(CH₂-4-F-C₆H₄)-]–CH(COOCH₂C₆H₅)H (L) |
| 101 | C₆H₅— | (H₃C)₂—CH—CH₂— | C₆H₅-CH₂— | —NH—CH[(CH₂)₄NHCOOCH₂C₆H₅](L) | —N-(CH₂)₄-CH(COOCH₂C₆H₅)H (L) |
| 102 | Cl₃CCH₂— | | H₅C₂— | —NH—CH[(CH₂)₃NHC(=NH)NH-NO₂](L) | —N-CH₂-S-CH(COOCH₂C₆H₅)H (L) |
| 103 | C₆H₅— | C₆H₅-CH₂— | C₆H₅-CH₂— | —NH—CH(CH₂-C₆H₅)— (L) | —N(CH₂-C₆H₄)-CH(COOCH₂C₆H₅)H (L) |
| 104 | thienyl | H— | H₅C₂— | —NH—CH(CH₂-CO-NH₂)—(L) | —N-(CH₂)₃-O-C₆H₅-CH(COOCH₂C₆H₅)H (L) |

-continued

| Example | R₁ | R₂ | R₃ | A | X |
|---|---|---|---|---|---|
| 105 | furan-2-yl-CH₂— | benzyl-CH₂— | benzyl-CH₂— | —NH—CH(L)—CH₂-(2-aminophenyl) | pipecolinate-type: —N(ring)—CH(H)(L)—COOCH₂-Ph |
| 106 | phenyl | thiophen-2-yl-CH₂— | H₅C₂— | —NH—CH(L)—CH₂-(N=CH-N-CH₂Ph) | —N(ring)—CH(H)(L)—COOCH₂-Ph |
| 107 | phenyl | benzyl-CH₂— | H₅C₂— | —NH—CH(L)—(CH₂)₂SCH₃ | —N(CH₂CH(Ph))—CH(H)(L)—COOCH₂-Ph |
| 108 | cyclohexyl | benzyl-CH₂— | benzyl-CH₂— | —NH—CH(L)—CH₂CH(CH₃)₂ | —N(ring)—CH(H)(L)—COOCH₂-Ph |
| 109 | phenyl | —(CH₂)₄— | benzyl-CH₂— | —NH—CH(L)—CH₂-(2,4-bis(OCH₂Ph)phenyl) | —N(ring)—CH(H)(L)—COOCH₂-Ph |

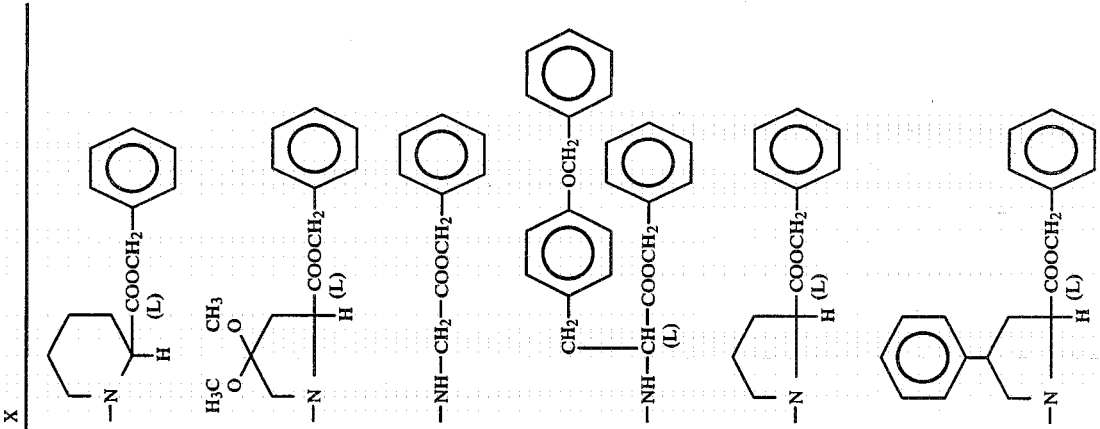

-continued
| Example | R₁ | R₂ | R₃ | A | X |
|---|---|---|---|---|---|
| 116 | 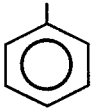 | 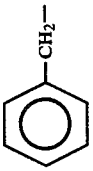 | 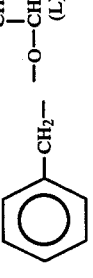 |  | 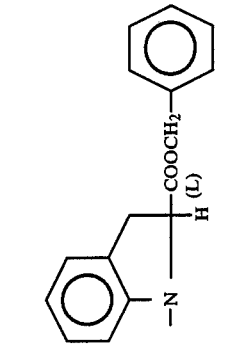 |
| 117 | 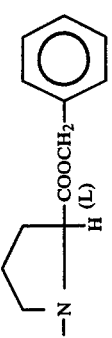 |  | H₅C₂— | —O—CH₂— |  |
| 118 |  | 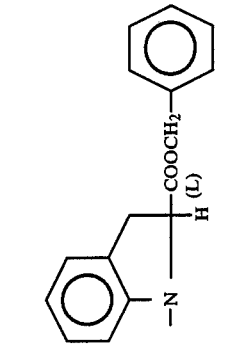 | 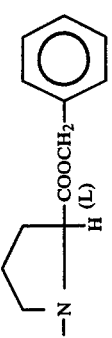 | 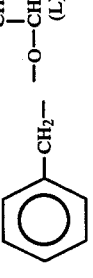 | 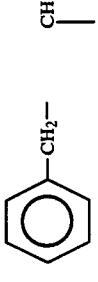 |
| 119 | H₅C₂— |  | 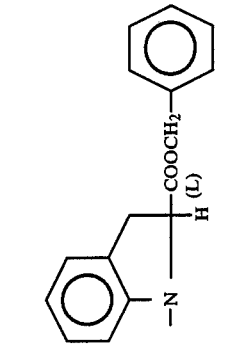 | 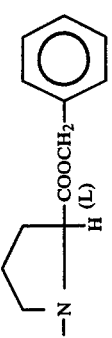 | 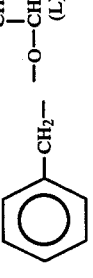 |
| 120 | 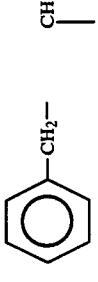 |  | 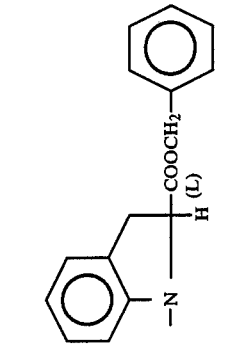 | 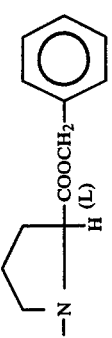 | 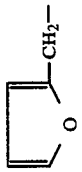 |

-continued
| Example | R₁ | R₂ | R₃ | A | X |
|---|---|---|---|---|---|
| 121 |  | —CH₂— | —CH₂— | —NH—CH—(L)<br>　　　│<br>　　　CH₃ |  |
| 122 |  | —CH₂— | —CH₂— | —NH—CH—(L)<br>　　　│<br>　　　CH₃ |  |

The R$_1$ protecting group shown in Example 114, the R$_2$ protecting group shown in Example 115, the R$_5$ protecting group shown in Example 113, and the R$_{23}$ protecting groups shown in Examples 101, 102, 106, 109, 110 and 120 are removed following completion of the reaction sequence. Also, the R$_3$ ester groups in Examples 96 to 122 and the R$_6$ ester groups in Examples 96 to 120 can be removed to yield the corresponding mono or diacid wich can then be converted to its salt form.

EXAMPLE 123

(S)-1-[[[2-(Benzoylamino)-3-phenylpropyl][(2,2-dimethyl-1-oxopropoxy)methoxy]phosphinyl]acetyl]-L-proline (a)

(S)-1-[[[2-(Benzoylamino)-3-phenylpropyl][(2,2-dimethyl-1-oxopropoxy)methoxy]phosphinyl]acetyl]-L-proline, phenylmethyl ester An equimolar mixture of triethylamine and chloromethyl pivalate are added to a solution of (S)-1-[[[2-(benzoylamino)-3-phenylpropyl]hydroxyphosphinyl]acetyl]-L-proline, phenylmethyl ester, prepared, for example, as set forth in Example 1(g), in dimethylformamide under argon. The mixture is stirred for several hours at room temperature, diluted with ethyl acetate, washed with water, brine, dried (MgSO$_4$), and evaporated. The crude product is chromatographed to give (S)-1-[[[2-(benzoylamino)-3-phenylpropyl][(2,2-dimethyl-1-oxopropoxy)methoxy]phosphinyl]acetyl]-L-proline, phenylmethyl ester.

(b)

(S)-1-[[[2-(Benzoylamino)-3-phenylpropyl][(2,2-dimethyl-1-oxopropoxy)methoxy]phosphinyl]acetyl]-L-proline A solution of the diester product from part (a) in methanol is added to a 10% palladium on carbon catalyst and the resulting mixture is shaken in a Parr hydrogenation apparatus for several hours. The catalyst is filtered off and the methanol is stripped from the filtrate. The crude product is chromatographed on silica gel to yield (S)-1-[[[2-(benzoylamino)-3-phenylpropyl][(2,2-dimethyl-1-oxopropoxy)methoxy]phosphinyl]acetyl]-L-proline.

EXAMPLES 124–128

Following the procedure of Example 123 but employing the alkylating agent shown in Col. I in place of the chloromethyl pivalate, one obtains the product listed in Col. II.

| Example | Col. I | Col. II |
|---|---|---|
| 124 | Br—CH$_2$—O—C(=O)—CH$_3$ | (S)—1-[[[2-(benzoylamino)-3-phenylpropyl][(acetyloxy)methoxy]phosphinyl]acetyl]-L-proline |
| 125 | Cl—CH(CH$_3$)—O—C(=O)—OC$_2$H$_5$ | (S)—1-[[[2-(benzoylamino)-3-phenylpropyl][1-(ethoxycarbonyloxy)ethoxy]phosphinyl]acetyl]-L-proline |
| 126 | Br-substituted 1,3-dihydro-3-oxo-1-isobenzofuranyl | (S)—1-[[[2-(benzoylamino)-3-phenylpropyl](1,3-dihydro-3-oxo-1-isobenzofuranyloxy)phosphinyl]acetyl]-L-proline |
| 127 | ClCH$_2$—O—C(=O)—C$_6$H$_5$ | (S)—1-[[[2-(benzoylamino)-3-phenylpropyl][(benzoyloxy)methoxy]phosphinyl]acetyl]-L-proline |
| 128 | Cl—CH(CH$_3$)—O—C(=O)—CH$_3$ | (S)—1-[[[2-(benzoylamino)-3-phenylpropyl][1-(acetyloxy)ethoxy]phosphinyl]acetyl]-L-proline |

Similarly, the alkylating agents of Examples 123 to 128 can be employed with the products of Examples 2 to 72, 78 to 93 and 95 to 120 to yield other compounds within the scope of this invention.

EXAMPLE 129

(S)-1-[[[2-(Benzoylamino)-3-phenylpropyl]hydroxyphosphinyl]acetyl]-L-proline, disodium salt Following the procedure of Example 1 but substituting AG-50W-X8 (Na+) for the lithium resin in part (h), one obtains (S)-1-[[[2-(benzoylamino)-3-phenylpropyl]hydroxyphosphinyl]acetyl]-L-proline, disodium salt.

This procedure can be employed in Examples 2 to 128 to give the corresponding mono or disodium salt. Similarly, by employing a potassium resin the corresponding mono or dipotassium salt is obtained.

EXAMPLE 130

1000 tablets each containing the following ingredients:

| | |
|---|---|
| (S)—1-[[[2-(Benzoylamino)-3-phenylpropyl]hydroxyphosphinyl]-L-proline, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (S)-1-[[[2-(benzoylamino)-3-phenylpropyl]hydroxyphosphinyl]acetyl]-L-proline, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containg 100 mg. of active ingredient.

In a similar manner, tablets containing 100 mg. of the product of any of Examples 1 to 128 can be prepared.

EXAMPLE 131

1000 tablets each containing the following ingredients:

| | |
|---|---|
| (S)—1-[[[2-(Benzoylamino-3-phenylpropyl][(2,2-dimethyl-1-oxopropoxy)methoxy]phosphinyl]acetyl]-L-proline, sodium salt | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the (S)-1-[[[2-(benzoylamino)-3-phenylpropyl][(2,2-dimethyl-1-oxopropoxy)methoxy]phosphinyl]acetyl]-L-proline, sodium salt, lactose and Avicel and then blending with the corn starch. Magnesium stearate is added and the dry mixture is compressed in a tablet press to form 1000 tablets each containing 50 mg. of active ingredient. The tablets are coated with a solution of Methocel E 15 (methyl cellulose) including as a color a lake containing yellow #6.

In a similar manner, tablets containing 50 mg. of the product of any Examples 1 to 122 and 124 to 128 can be prepared.

EXAMPLE 132

Two-piece #1 gelatin capsules each containing 100 mg. of (S)-1-[[[2-(benzoylamino)-4-methylpentyl]hydroxyphosphinyl]acetyl]-L-proline, disodium salt are filled with a mixture of the following ingredients:

| | |
|---|---|
| (S)—1-[[[2-(Benzoylamino-4-methylpentyl]hydroxyphosphinyl]acetyl]-L-proline, disodium salt | 100 mg. |
| Magnesium stearate | 7 mg. |
| Lactose | 193 mg. |
| | 300 mg. |

In a similar manner, capsules containing 100 mg. of the product of any of Examples 1 and 3 to 129 can be prepared.

EXAMPLE 133

An injectable solution is prepared as follows:

| | |
|---|---|
| 1-[[[2-(Benzoylamino-4-phenylbutyl]hydroxyphosphinyl]acetyl]-L-proline, disodium salt | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1, 2 and 4 to 129.

EXAMPLE 134

1000 tablets each containing the following ingredients:

| | |
|---|---|
| (S)—1-[[[2-(Benzoylamino)-3-phenylpropyl]hydroxyphosphinyl]acetyl]-L-proline, disodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the (S)-1-[[[2-(benzoylamino)-3-phenylpropyl]hydroxyphosphinyl]acetyl]-L-proline, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 2 to 128.

What is claimed is:

1. A compound of the formula

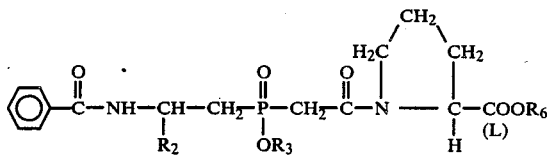

wherein

R₂ is phenylmethyl; and

R₃ and R₆ are the same and each is hydrogen, sodium, potassium, or lithium.

2. The compound of claim 1, (S)-1-[[[2-(benzoylamino)-3-phenylpropyl]hydroxyphosphinyl]acetyl]-L-proline, dilithium salt.

3. A composition useful for treating hypertension comprising a pharmaceutically acceptable carrier and a hypotensive agent or pharmaceutically acceptable salt thereof of the formula

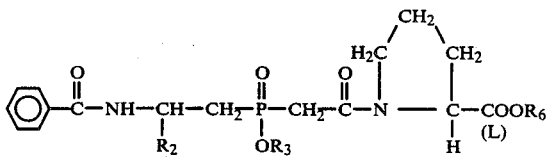

wherein R₂, R₃ and R₆ are as defined in claim 1.

4. The method of alleviating hypertension in a mammalian specie which comprises administering an effective amount of the composition of claim 3.

5. A compound of the formula

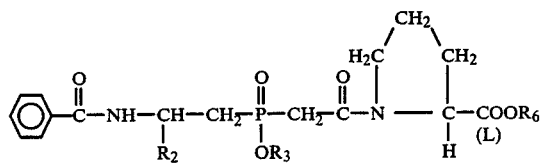

wherein
  R₂ is phenylethyl; and
  R₃ and R₆ are the same and each is hydrogen, sodium, potassium or lithium.

6. A composition useful for treating hypertension comprising a pharmaceutically acceptable carrier and a hypotensive agent or pharmaceutically acceptable salt thereof of the formula

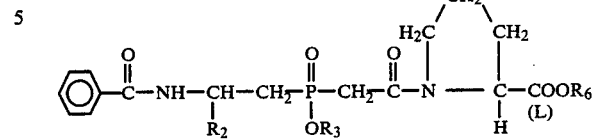

wherein R₂, R₃ and R₆ are as defined in claim 5.

7. The method of alleviating hypertension in a mammaliam specie which comprises administering an effective amount of the composition of claim 6.

* * * * *